United States Patent [19]
Packard

[11] Patent Number: 5,938,634
[45] Date of Patent: Aug. 17, 1999

[54] PERITONEAL DIALYSIS SYSTEM WITH VARIABLE PRESSURE DRIVE

[75] Inventor: Warren J. Packard, Palo Alto, Calif.

[73] Assignee: Baxter International Inc., Deerfield, Ill.

[21] Appl. No.: 08/702,878

[22] Filed: Aug. 23, 1996

Related U.S. Application Data

[60] Provisional application No. 60/003,452, Sep. 8, 1995.

[51] Int. Cl.$^6$ .................................................. A61M 1/00
[52] U.S. Cl. ............................................................. 604/29
[58] Field of Search ................................. 604/29, 30, 67, 604/132, 141; 417/395; 128/DIG. 12, DIG. 13

[56] References Cited

U.S. PATENT DOCUMENTS

| | | | |
|---|---|---|---|
| 3,709,222 | 1/1973 | DeVries | 128/213 |
| 4,158,530 | 6/1979 | Bernstein | 417/389 |
| 4,479,760 | 10/1984 | Bilstad et al. | 417/395 |
| 4,613,327 | 9/1986 | Tegrarian et al. | 604/141 |
| 4,634,430 | 1/1987 | Polaschegg | 604/141 |
| 4,976,162 | 12/1990 | Kamen | 73/865.9 |
| 5,088,515 | 2/1992 | Kamen | 137/15 |
| 5,350,357 | 9/1994 | Kamen et al. | 604/29 |

FOREIGN PATENT DOCUMENTS

| | | |
|---|---|---|
| 0 206 195 A2 | 12/1986 | European Pat. Off. . |
| 0402505 | 12/1990 | European Pat. Off. . |
| 0459647 | 12/1991 | European Pat. Off. . |
| 9013795 | 11/1990 | WIPO . |
| 9420158 | 9/1994 | WIPO . |

*Primary Examiner*—Manuel Mendez
*Attorney, Agent, or Firm*—Charles R. Mattenson; Thomas S. Borecki; Richard P. Beem

[57] ABSTRACT

A variable pressure drive peritoneal dialysis system has a pneumatic pressure system for purging and controlling a flow of dialysate through a disposable dialysate cassette of a disposable dialysate delivery set. The pneumatic pressure system has a variable-opening flow proportional valve for supplying air at selected profiled pressure or vacuum to a pneumatic interface. The disposable dialysate cassette has a diaphragm pump actuable by the profiled air pressure or vacuum to move dialysate to and from a patient via the disposable dialysate delivery set at a desired profiled dialysate pressure.

23 Claims, 37 Drawing Sheets

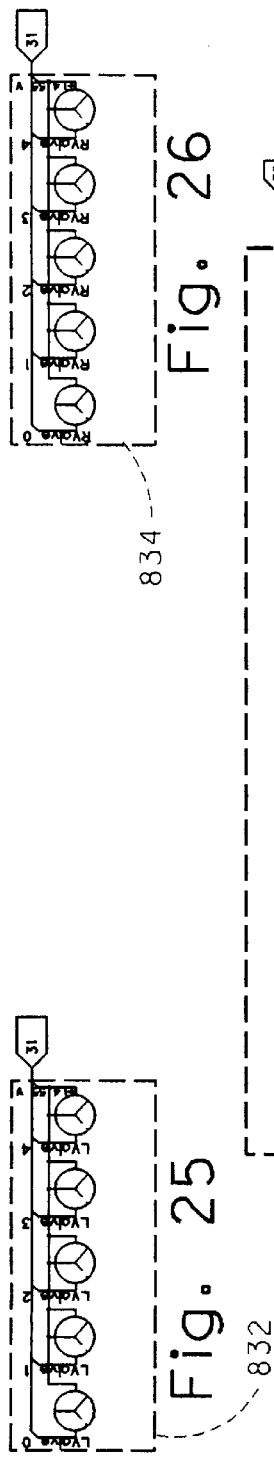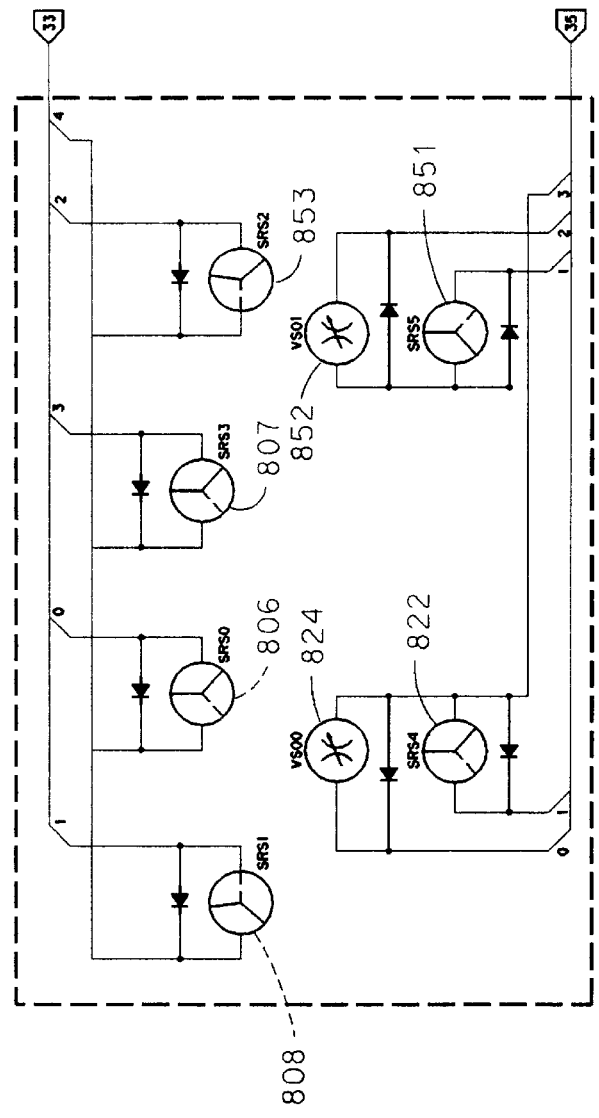

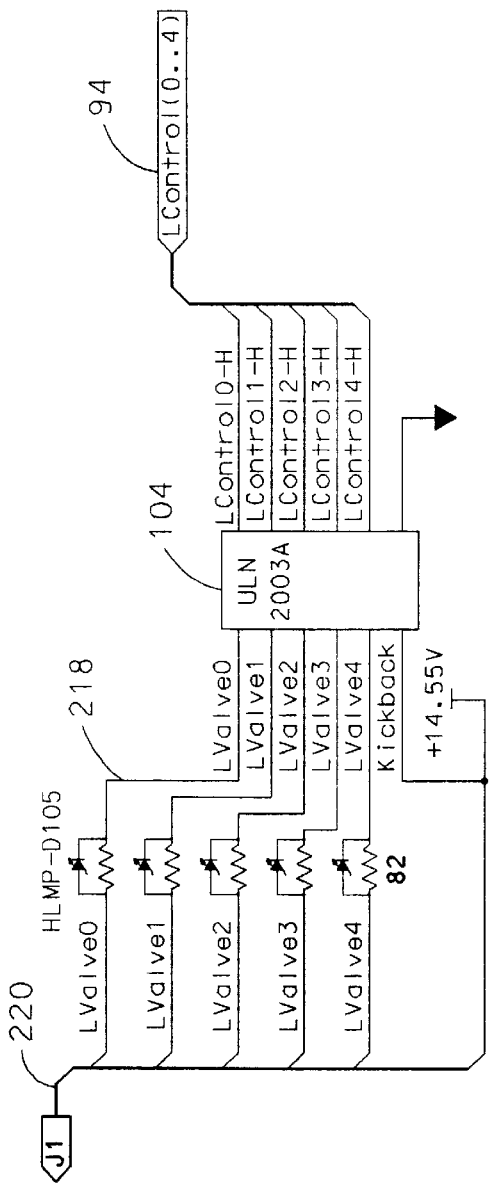
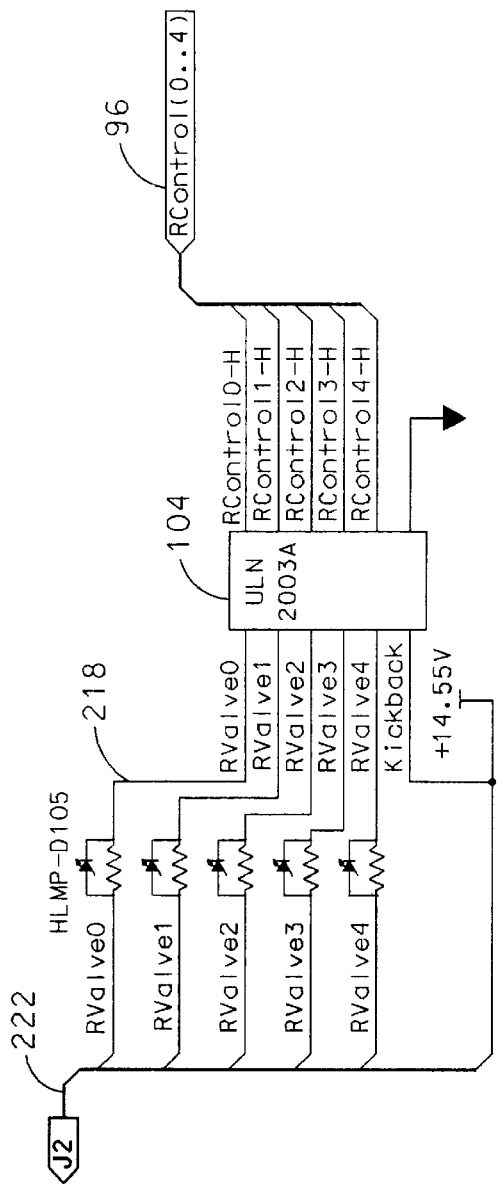

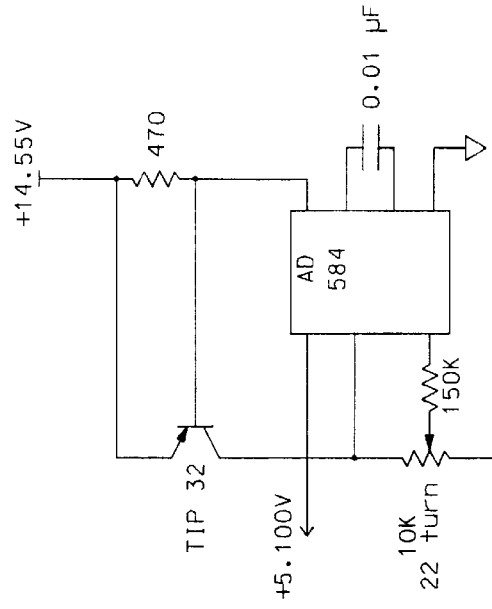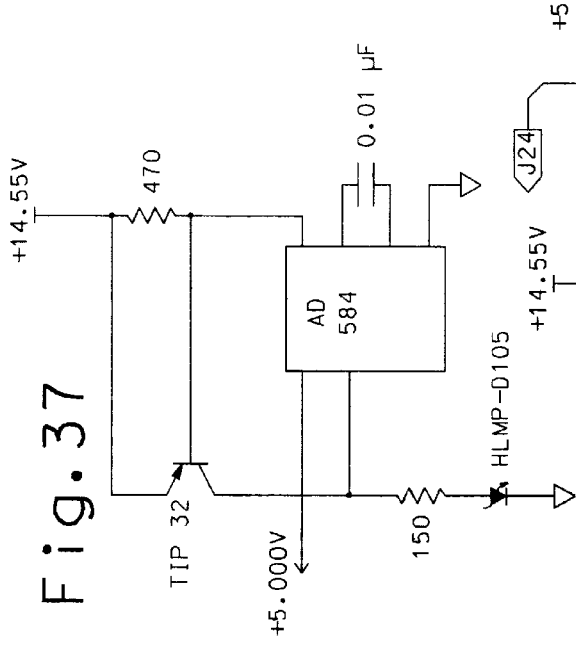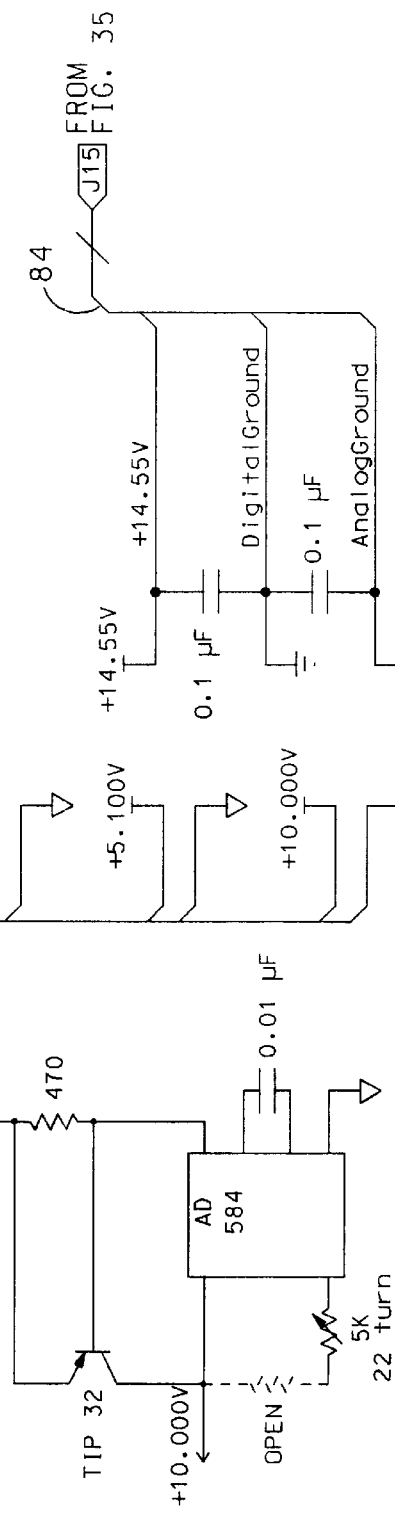

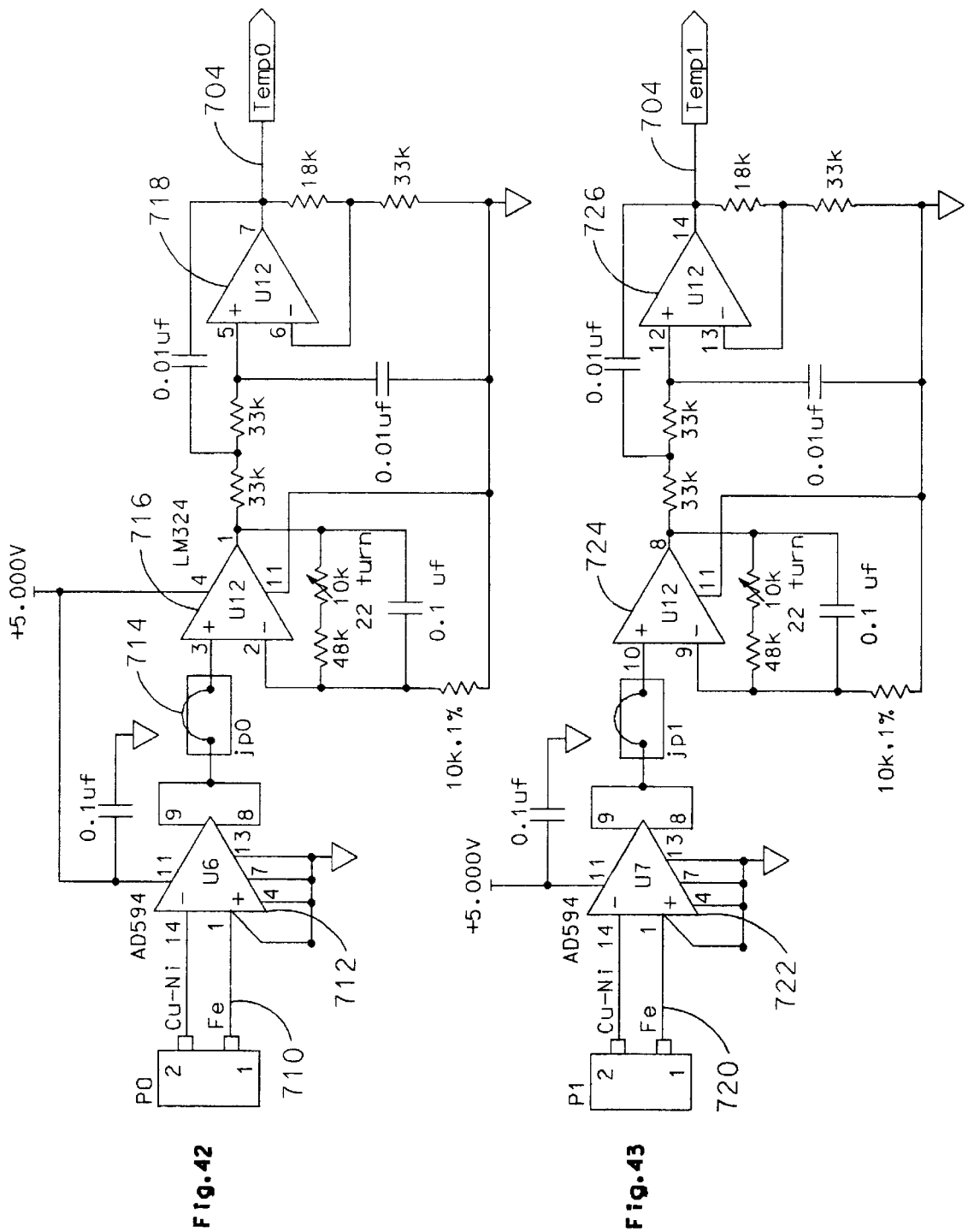

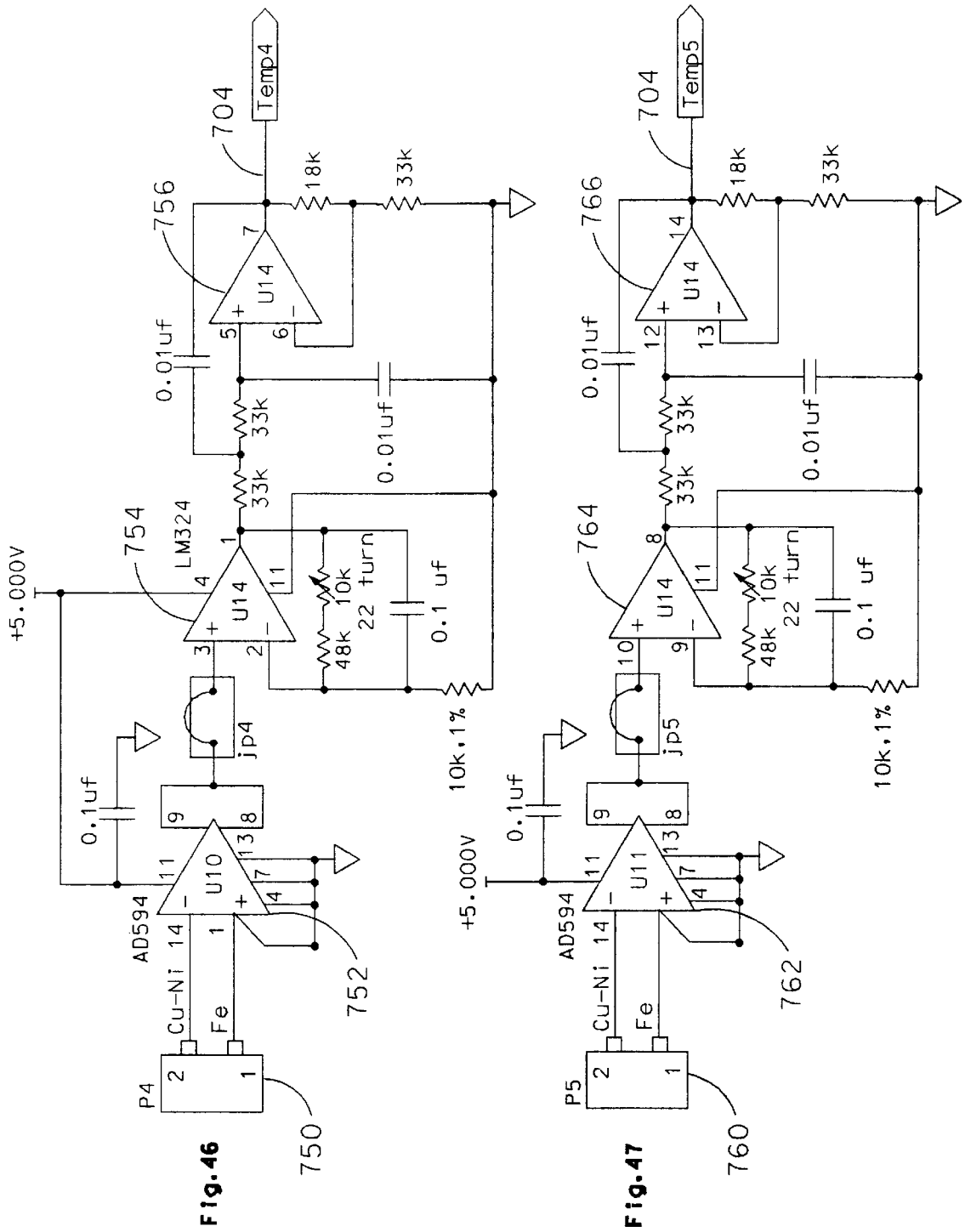

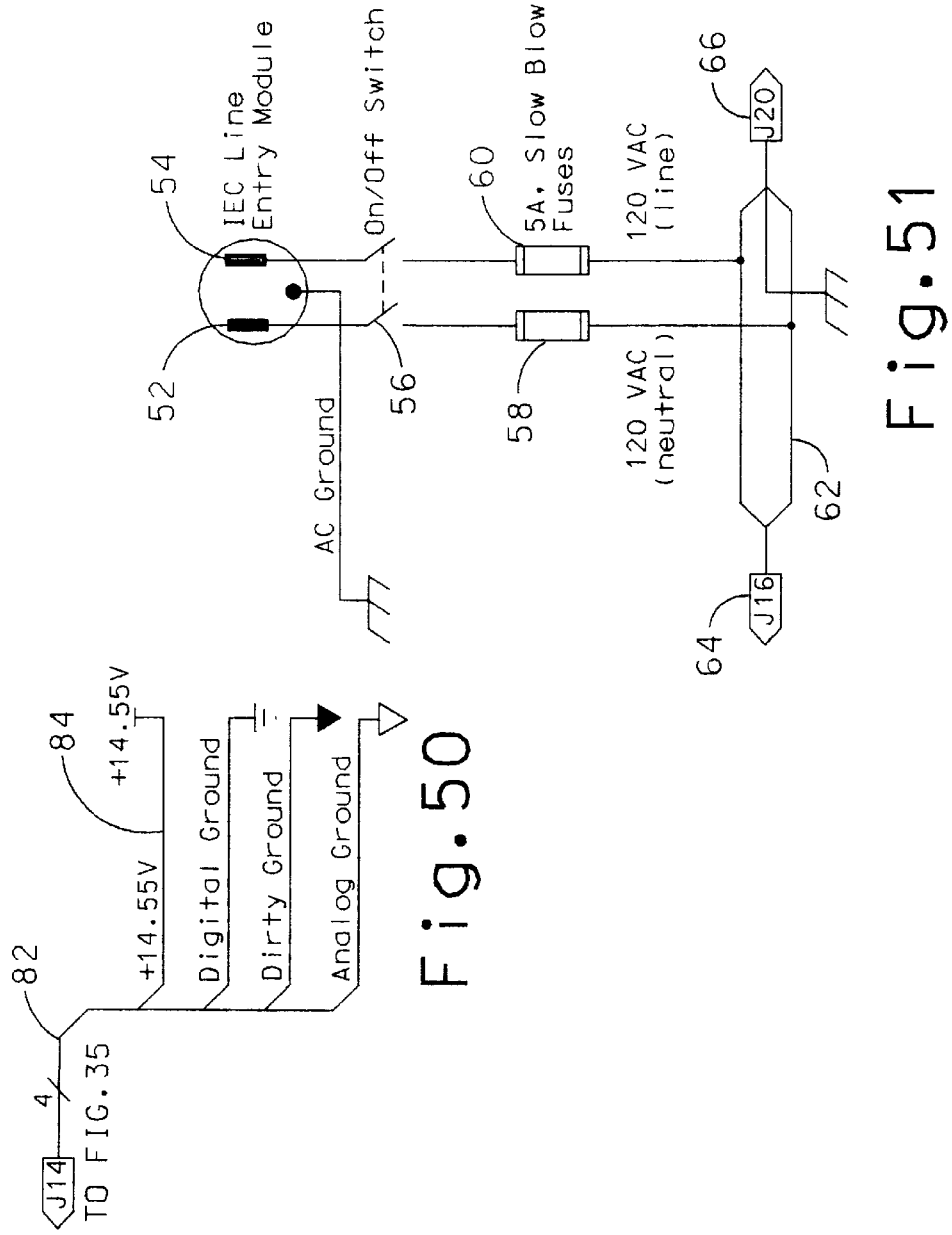

5,938,634

PERITONEAL DIALYSIS SYSTEM WITH VARIABLE PRESSURE DRIVE

CROSS REFERENCE TO RELATED APPLICATION

This application claims the benefit of priority of prior U.S. provisional application, application no. 60/003,452, filed Sep. 8, 1995.

BACKGROUND OF THE INVENTION

This invention relates to an improved automated peritoneal dialysis (APD) system for use in medical treatment involving administration of parenteral fluids as in peritoneal dialysis.

It is known that patients experiencing partial or complete renal failure are often helped by peritoneal dialysis regimens. Two types of peritoneal dialysis are commonly available. Manual peritoneal dialysis allows a dialysate fluid from a bag to be gravity fed through a tube into an indwelling catheter extending into a patient's peritoneal cavity. Automated peritoneal dialysis may be carried out as set forth in U.S. Pat. No. 5,350,357 to Kamen et al. The Kamen et al. automated peritoneal dialysis system is an attractive system for home use in that it provides a small footprint system while allowing a patient to dialyze himself or herself several times in the course of a night with fresh dialysate contained in multiple bags. That automated system includes a heater for raising the temperature of the dialysate from ambient to body temperature and includes a disposable liquid delivery set for mating with a cycler which causes pneumatic force to be supplied to selected portions of the delivery set to pump dialysate through the delivery set from the dialysate bags to the heater bag, from the heater bag to the patient and from the patient to a drain. Fresh peritoneal dialysis solution is infused into the patient's peritoneal cavity wherein by osmotic exchange wastes such as solutes of sodium and chloride ions, urea, creatinine and water are transferred to the dialysate solution in the peritoneal cavity and are then removed from the peritoneal cavity. The Kamen et al. system proceeds through a succession of fill, dwell, and drain phases that follow one after another and one of the advantages of the system is provided by the fact that the system can emulate either fixed height or different head height conditions regardless of the actual head height. The system is able to switch rapidly during a given peritoneal dialysis procedure between a relatively low pressure mode and a high pressure mode, with the low pressure being used during patient infusion and drain procedures and the high pressure mode being used to move dialysate through circuits not directly connected to the patient. Unfortunately, the system requires a number of high pressure and low pressure reservoirs therein for supply of pneumatic force to a pneumatic interface, which in turn requires a large number of valves associated with reservoirs. The multiple reservoirs and numerous valves result in a relatively large system in which there is only a limited choice of pneumatic pressure levels available for actuating the dialysate pumps, and there is no capability to obtain selectable pressure versus time profiles, e.g., to ramp up or to ramp down the pneumatic pressure as quickly or as slowly as may be desirable for a given dialysis regimen.

The Kamen et al. system operates at unmodulated pneumatic supply pressure levels which may prove to be disadvantageous in certain patient regimens.

Thus, it is desirable to be able to provide an automated peritoneal dialysis system having a cycler capable of delivering a wide range of pneumatic pressures and pressure profiles to a cassette of a disposable dialysate through a liquid delivery set which the dialysate solution may be moved to and from the patient.

SUMMARY OF THE INVENTION

A system for performing automated peritoneal dialysis by delivering dialysate to the patient and draining spent dialysate includes an automated peritoneal dialysis apparatus or cycler, having an electrical controller for supplying control signals to a pneumatic supply or distribution system. The pneumatic supply system includes one or more flow proportional valves for controlling air pressure supplied to a cassette interface.

This eliminates the need for many of the reservoirs of the type used in the prior art systems because the flow proportional valve modulates the air pressure received from the compressor or vacuum pump. The elimination of reservoirs, in turn, simplifies the pneumatic distribution system and reduces the number of valves needed in the system. The use of one or more flow proportional valves also allows the drive pressure to the diaphragm pumps of a dialysate cassette to be profiled thereby providing for maximum flexibility in available treatment regimens and for improved patient safety and comfort. The small number of reservoirs and reduced number of valves used in the present system allows it to be compact and quiet.

The cassette interface receives the disposable dialysate routing and pumping cassette of a disposable dialysate delivery set. The disposable dialysate delivery set is connected to the cycler at the cassette interface and is driven by the air pressure delivered at the cassette interface to pump dialysate in accordance with a dynamic pressure profile between a patient and dialysate supply bags and a drain at a wide range of dialysate pressures to provide patient safety and comfort during dialysate fill and dialysate dwell procedures, as well as dialysate drain procedures.

It is a principal object of the present invention to provide an automated peritoneal dialysis system for providing dialysate at a variety of pressures to a patient to maintain patient safety and comfort.

Other objects of the present invention will become obvious to one of ordinary skill in the art on perusal of the following specifications and claims in light of the accompanying drawings.

BRIEF DESCRIPTION OF THE DRAWINGS

FIGS. 24 through 28 are schematic diagrams of the electrical control and power distribution system for a plurality of valves, a compressor and a vacuum pump of a second embodiment of the APD system;

FIG. 30 is a schematic diagram of a portion of the control system of the first embodiment for the pneumatic valves which operate the liquid valves in the disposable cassette for controlling the flow of dialysate to the left diaphragm pump of the disposable cassette;

FIG. 31 is a schematic diagram of a portion of the control system of the first embodiment for the pneumatic valves which operate the liquid valves in the disposable cassette for controlling the flow of dialysate to the right diaphragm pump of the disposable cassette;

FIG. 37 is a schematic diagram of a portion of a sensor board shown in FIG. 29 and having a precision voltage reference for converting 14.55 volts DC to 5.000 volts DC;

FIG. 38 is a schematic diagram of a portion of the sensor board having a precision voltage reference which converts 14.55 volts DC to 5.100 volts DC;

FIG. 39 is a schematic diagram of a portion of the sensor board having a precision voltage reference which converts 14.55 volts to 10.000 volts;

FIG. 40 is a schematic diagram of a portion of the sensor board showing a cable header and three precision voltage references;

FIG. 41 is a schematic diagram of a portion of the sensor board showing a cable header for providing DC power at 14.55 volts to the sensor board;

FIGS. 42 through 47 are schematic diagrams of temperature sensing circuits having thermocouples and being mounted on the sensor board;

FIG. 50 illustrates a power supply output header;

FIG. 51 is a schematic diagram of an AC entry module;

FIG. 52 is a schematic diagram of a DC power supply;

FIG. 53 is a schematic diagram of an analog sensor input circuit having a plurality of pressure sensors and an associated interface for communicating signals corresponding to the pressures sensed by the pressure transducers as well as heater bag temperatures and the like;

DETAILED DESCRIPTION OF THE PREFERRED EMBODIMENTS

Figure 1:
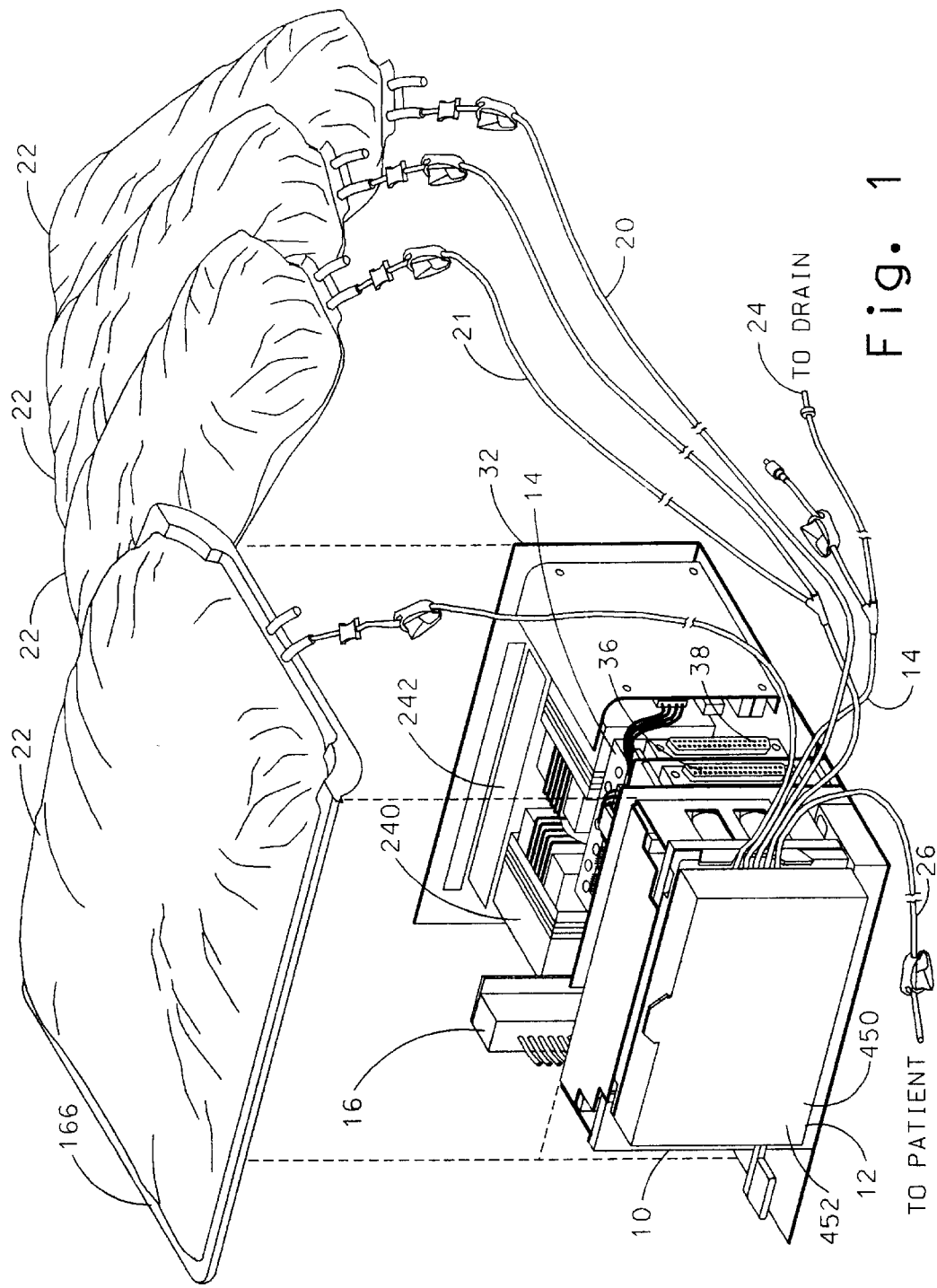
FIG. 1 is a perspective view of an automated peritoneal dialysis (APD) system embodying the present invention and having an APD apparatus or cycler and a liquid delivery set.
Figure 2:
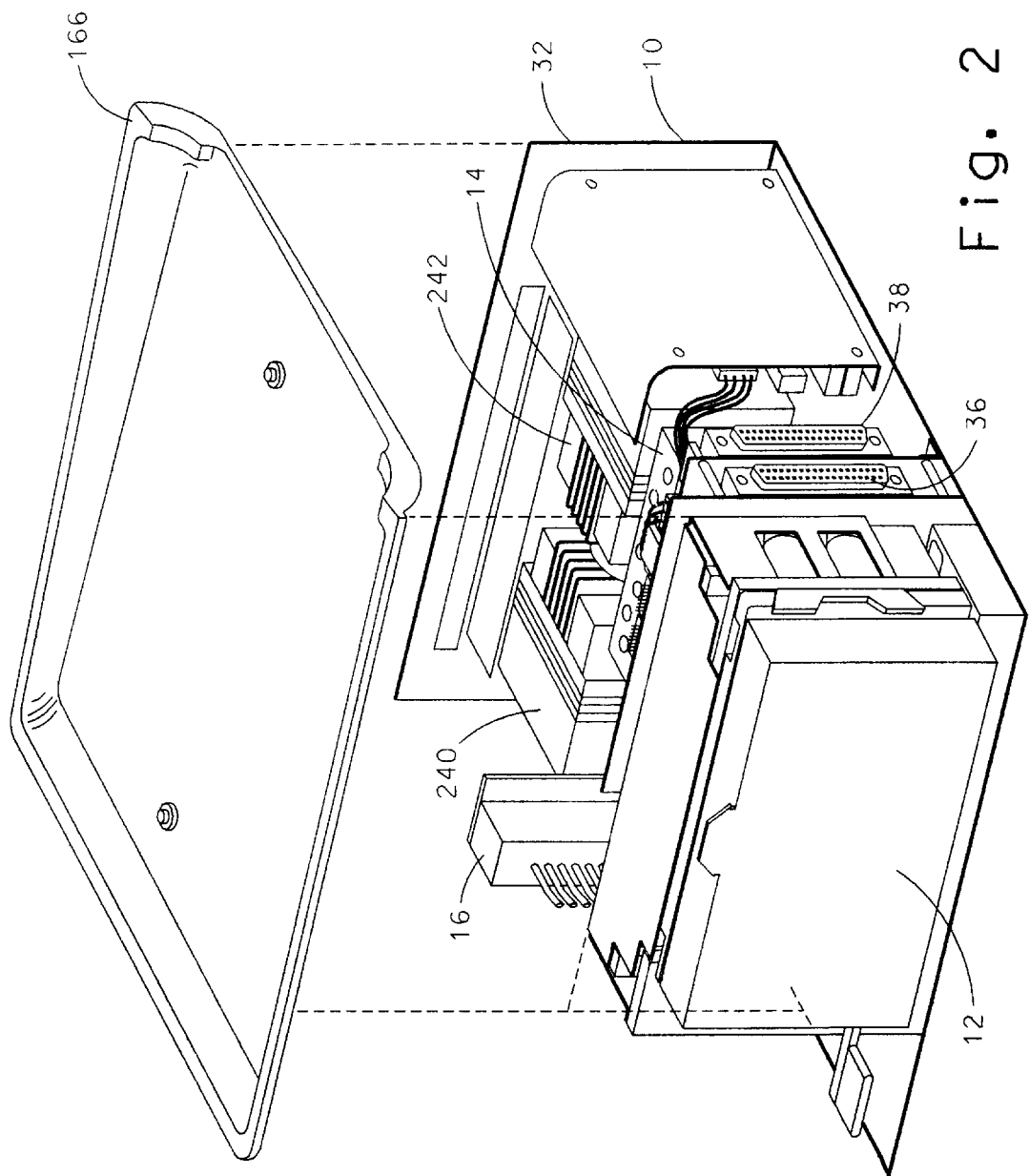
FIG. 2 is a perspective view of the APD system shown in FIG. 1.
Figure 3:
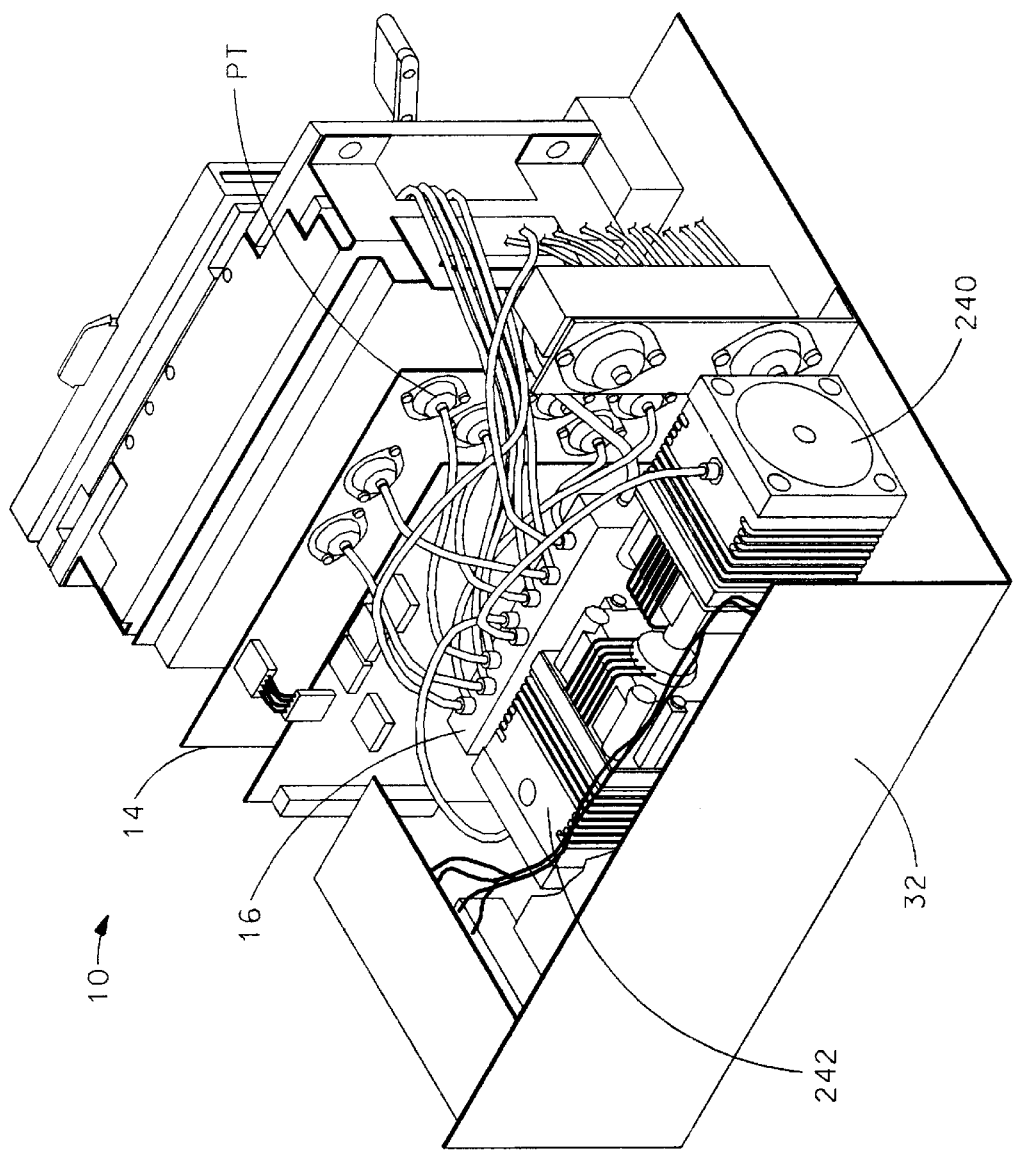
FIG. 3 is a rear perspective view of the APD system shown in FIG. 1.
Figure 4:
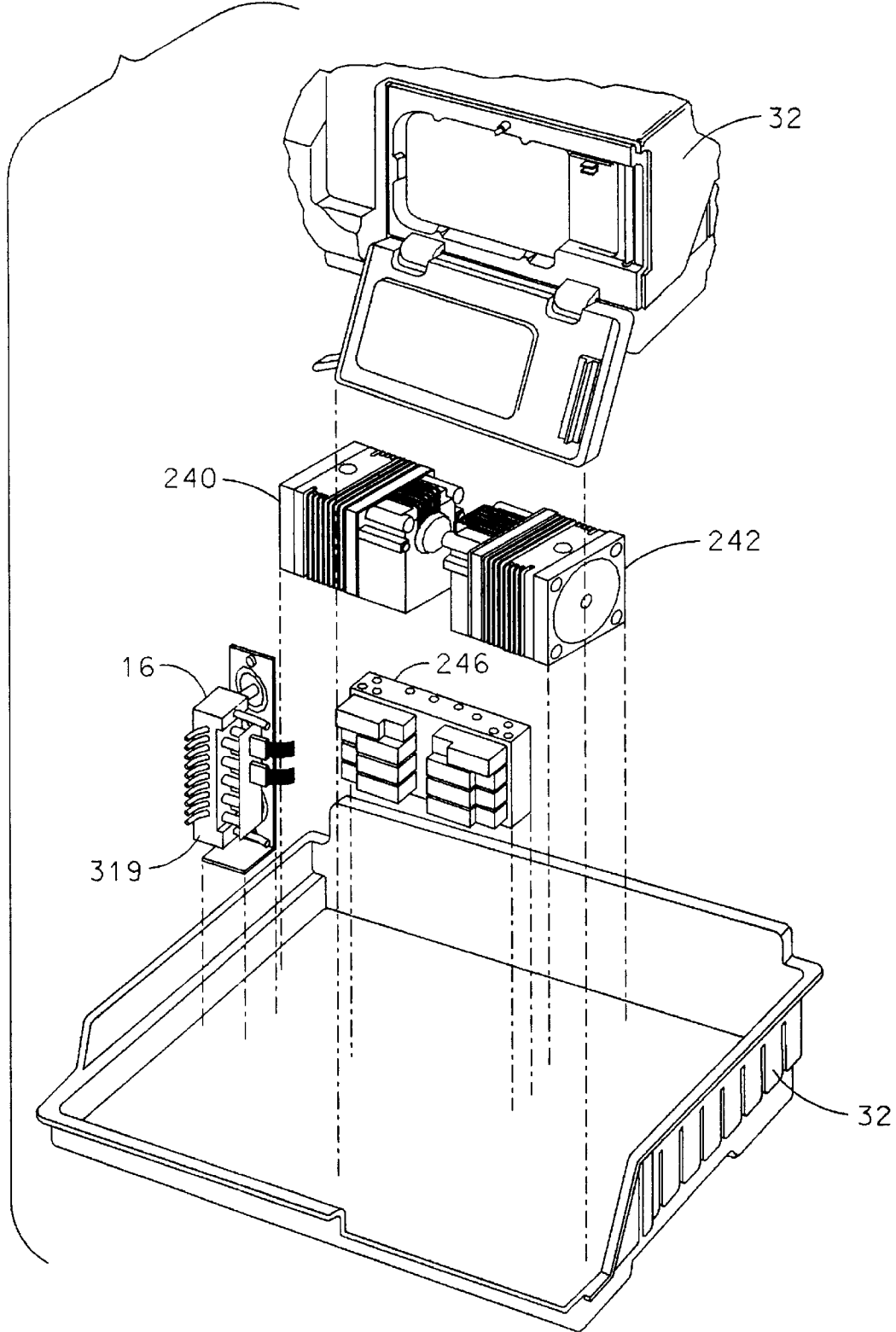
FIG. 4 is a partially exploded perspective view of the APD system shown in FIG. 1 showing a compressor, a vacuum pump, a plurality of pneumatic valves and a disposable dialysate cassette holder.
Figure 5:
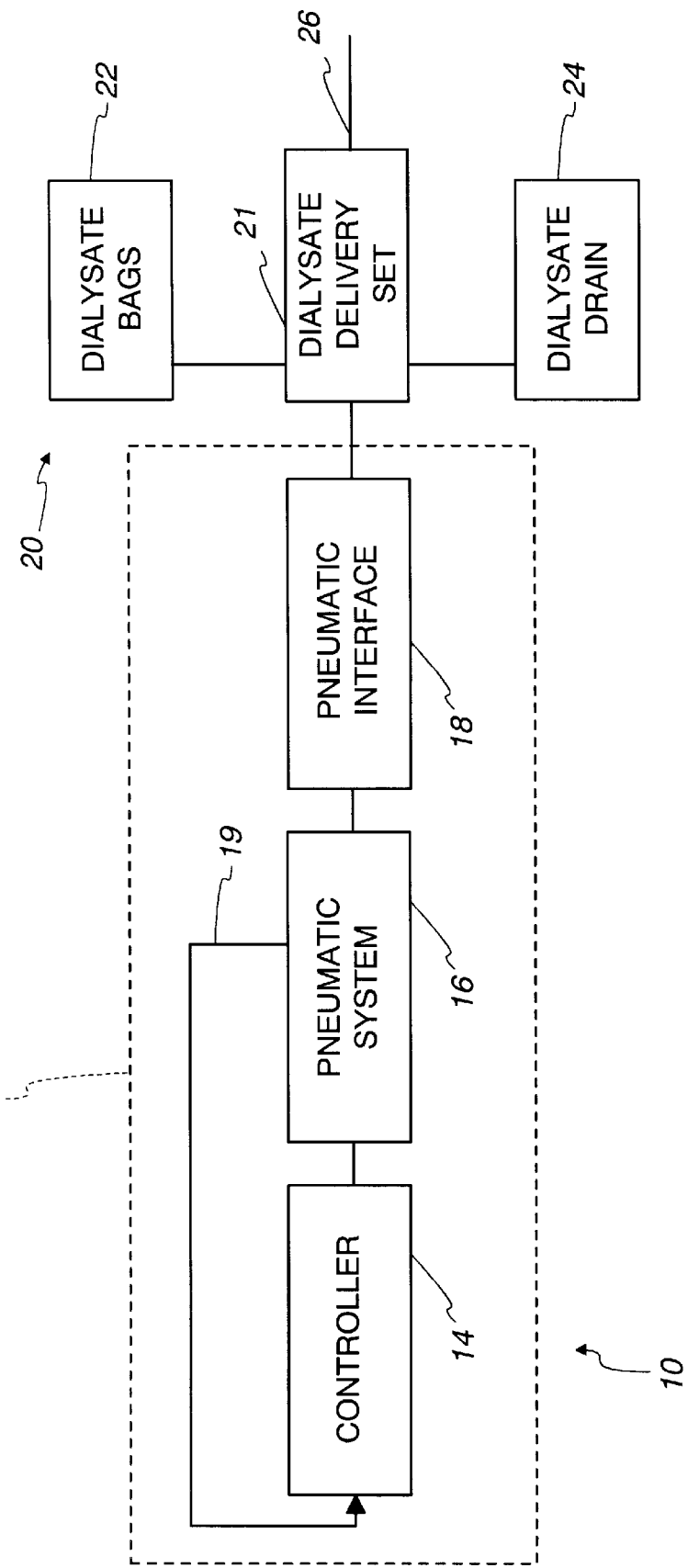
FIG. 5 is a block diagram of the automated peritoneal dialysis system shown in FIG. 1.

Referring now to the drawings, and especially to FIGS. 1 through 6, an automated peritoneal dialysis (APD) system is generally shown therein and identified by numeral 10. The APD system 10 includes an automated peritoneal dialysis apparatus or cycler 12 comprising an electrical controller 14 coupled to supply control and drive signals to a pneumatic supply or distribution system 16. The pneumatic distribution system 16 supplies air at various pressures to a pneumatic cassette interface 18. A feedback loop 19 provides feedback signals from the pneumatic distribution system 16 to the controller 14.

A disposable liquid or dialysate delivery system 20 includes a disposable liquid or dialysate delivery set 21 which may be coupled to the pneumatic cassette interface 18. A plurality of dialysate bags 22 may be connected to the disposable dialysate delivery set 21 for supply of dextrose-based dialysate through the disposable dialysate delivery set 21. The delivery set 21 includes a disposable dialysate cassette 23 for connection to a dialysate drain 24 and through a patient tube 26 to a catheter 27 connected to a patient 28.

The cycler 12 has a housing 32 which holds the electrical controller 14, the pneumatic supply system and the pneumatic cassette interface 18.

Figure 29:
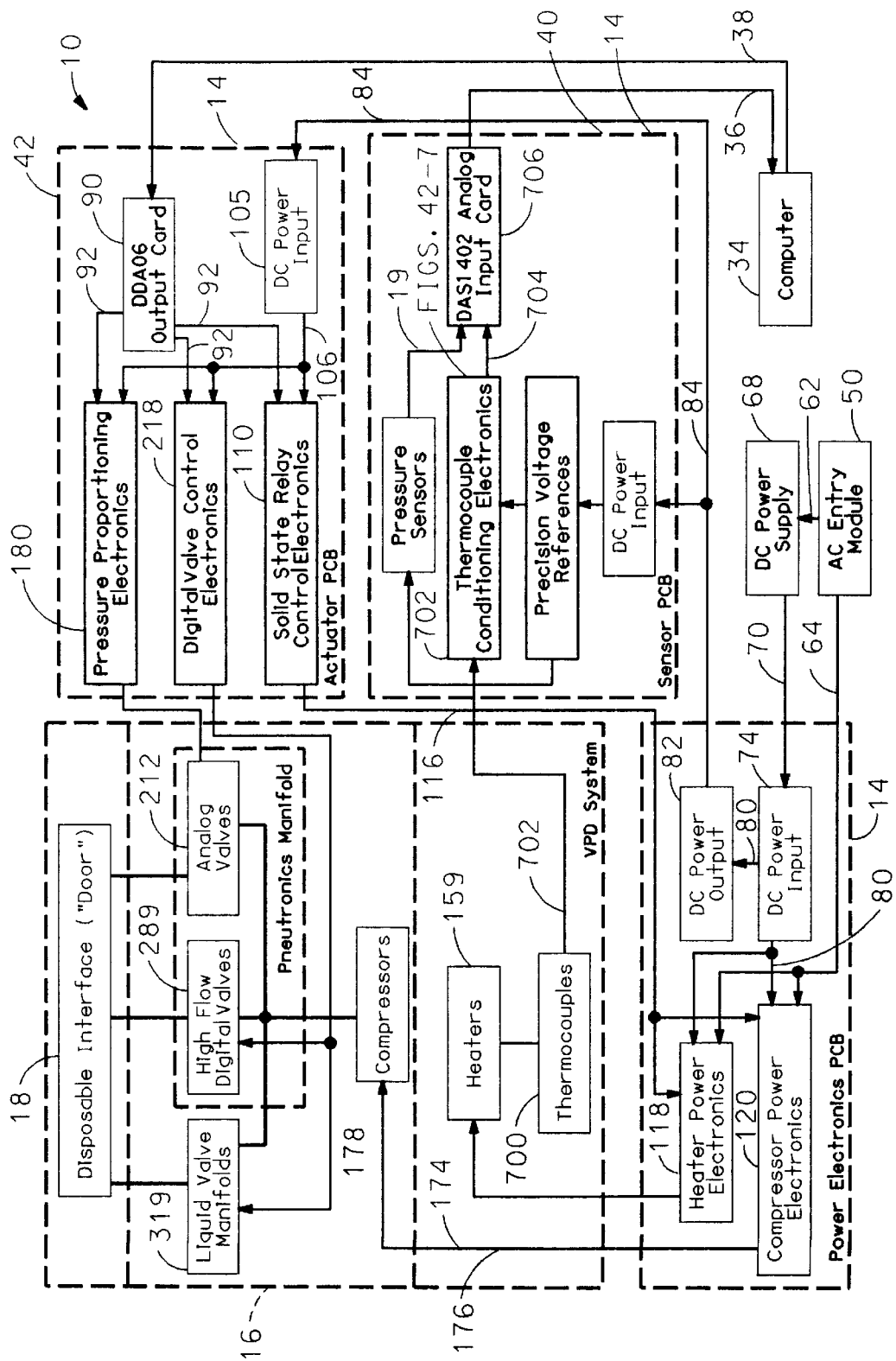
FIG. 29 is a block diagram of a controller of the APD system shown in FIG. 1.

The controller 14, as may best be seen in FIGS. 29 and 51, receives alternating current electric power from a suitable source through.

The electrical controller 14 includes a computer 34 which may either comprise an embedded microprocessor which could be included on a circuit board or the like within a housing 32 or a separate stand-alone type personal computer. The computer 34 may comprise an IBM compatible personal computer including a microprocessor connected to a one or more system buses, a random access memory for storing programming instructions and data to be operated upon, a hard disk connected to the system bus for storing program and data information in a permanent fashion; a floppy disk drive is provided for the input and output of programs and data to the computer system. A video display monitor is connected to the bus of the computer through a video controller module. The video display monitor displays control and prompting indications related to the operation of the automated peritoneal dialysis system 10. A keyboard is included for input of commands and for interrogation of the system 10. The keyboard may be employed for responding to prompts appearing on the video display terminal. The keyboard also sends commands to other portions of the computer 34 causing it to control the rest of the electrical controller 14 in such a way as to cause a dialysate fill operation to occur, to cause the dialysate dwell operation including a heater bag fill operation to occur, or to cause a dialysate drain operation to occur. As an alternative to a keyboard, a control panel for inputting commands and for interrogation of the system 10 may be mounted directly on or proximate to the cycler housing and connected to the computer, which alternative may be advantageous if an embedded microprocessor is used in the system.

The computer 34 receives digital information from other portions of the controller through an RS-232 line 36 and outputs digital signals through an RS-232 line 38. The RS-232 input line 36 receives digital signals from a sensor board 40 and the computer supplies command information to an actuator board 42.

Figures 48, 49:
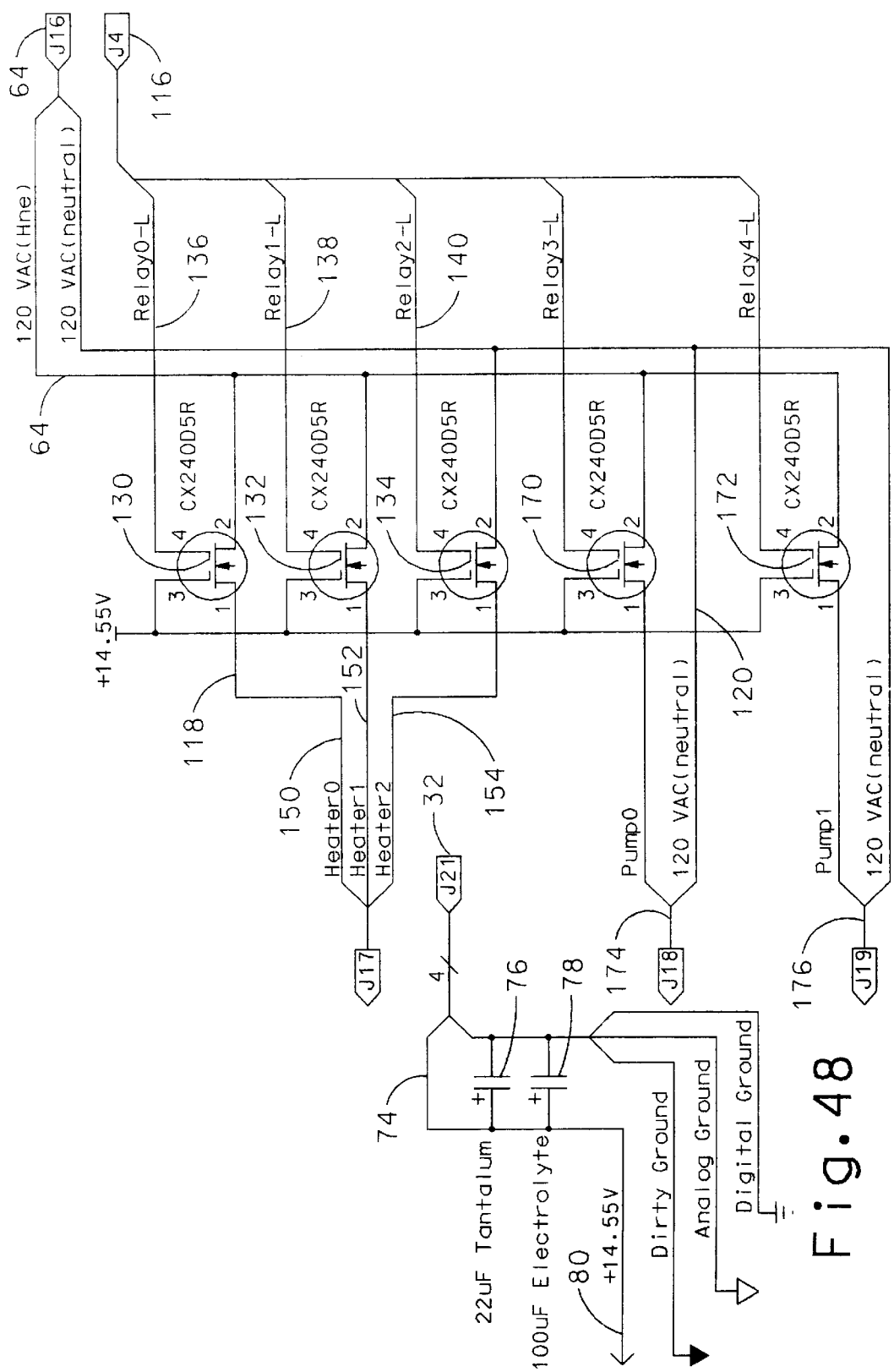
FIG. 48 is a schematic diagram of a DC power input mounted on a power board shown in FIG. 29.
FIG. 49 is a schematic diagram of a power supply for heater and compressor power electronics, also mounted on the power board.

The electrical controller 14 has an AC entry module 50 having a pair of alternating current line input terminals 52 and 54 for receiving alternating current from a suitable source, as may best be seen in FIG. 51. The alternating current is supplied via terminals 52 and 54 to a switch 56 which, when closed, supplies current through a pair of fuses 58 and 60 to an AC bus 62. A pair of power takeoff jacks 64 and 66 are connected to the AC bus 62. A DC power supply 68 receives the alternating current input at the jack 66 and outputs DC power at a DC bus 70 through a jack 72 as shown in FIGS. 29 and 52. The direct current is fed through the jack 72 to a DC power input module 74 as shown in FIGS. 29 and 48. A tantalum capacitor 76 and an electrolytic capacitor 78 remove ripple from the DC power and a positive 14.55 volts potential is supplied through a lead 80 to other portions of the controller 14. DC power also is output through a DC power module 82, shown in FIGS. 29 and 50, and the positive 14.55 volts potential is supplied on a lead 84 to other portions of the controller.

When the user commands the computer 34 to run a dialysis procedure the computer supplies device command signals via the serial communication line 36 to a digital to analog converter card, in this embodiment a Keithley-Metrabyte DDA06 output card 90. The digital to analog converter card 90 converts the command signals into analog compressor, heater and pneumatic valve control signals. The analog control signals are carried by a control signal bus 92 as may best be seen in FIG. 36. The control signal bus 92 is connected to supply the analog control signals to a left valve control signal bus 94, a right valve control signal bus 96, a flow proportional valve control signal bus 98, a routing valve control signal bus 100 and a combination heater and compressor control signal bus 102.

Figure 33:
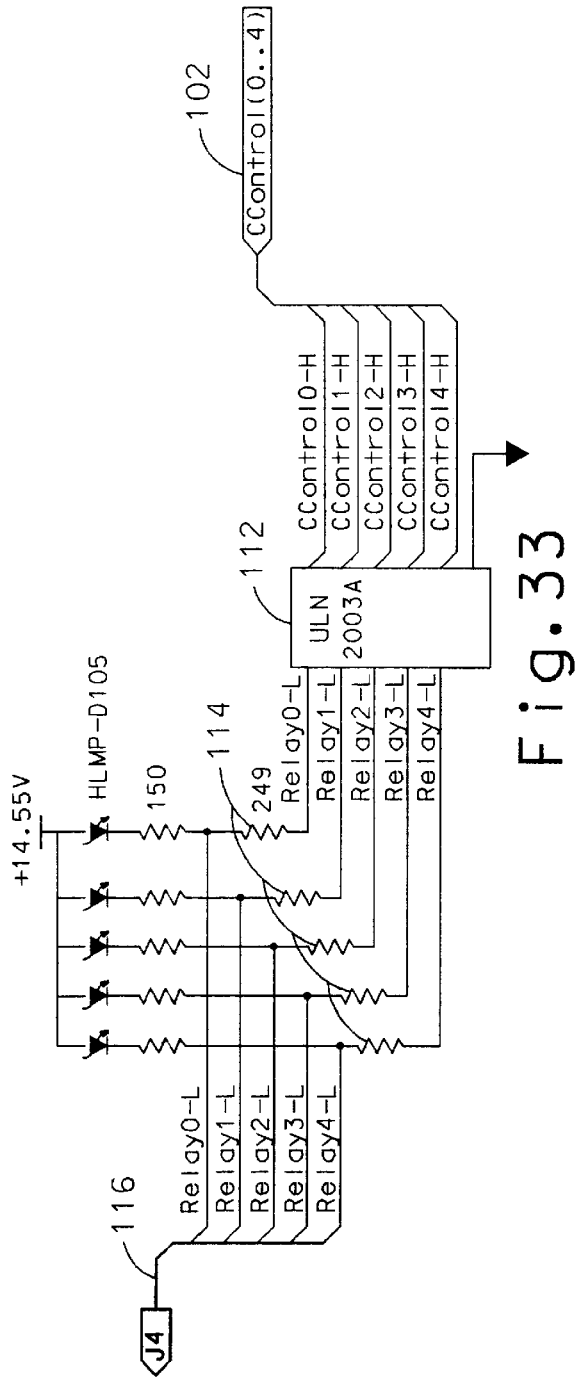
FIG. 33 is a schematic diagram of solid-state relay control electronics for providing power control signals.

When the automated peritoneal dialysis system 10 is switched on its commands are produced by the computer 34. A solid state relay control electronics module 110 coupled to receives signals from the compressor and heater control bus 102. As shown in FIG. 33, it receives the signals and passes them through a ULN 2003A driver 112 and feeds them through a plurality of load resistors 114 to a relay output bus 116 coupled to a heater power electronics module 118 and a compressor power electronics module 120.

The heater power module 118 and the compressor power module 120 are energized by DC power through a DC power supply bus 80, as shown in FIGS. 29 and 49. AC power is provided through the AC bus 64 to energize both the heater power module 118 and the compressor power module 120. Three heater power field effect transistors 130, 132 and 134 are coupled to respective gate control leads 136, 138 and 140 connected through bus 116. The heater power transistors 130 through 134 control AC power through heater power supply lines 150, 152 and 154 to energize either or both of a pair of dialysate bag heaters 160 and 162 connected thereto. The heaters 160 and 162 are in good heat conduction relationship with a heat conductive aluminum heater bag pan 166 upon which is supported one of the dialysate bags 22, the heater dialysate bag 22 which is to be heated to about 37° C. or body temperature of a human being.

Alternating current power is also supplied by the alternating current line 64 to a pair of pneumatic drive power field effect transistors 170 and 172 that connect AC power through compressor leads 174 and 176 to a pair of compressors 178. The pair of compressors 178 is part of the pneumatic control system 16 and supplies above and below atmospheric pressure air to other portions of the pneumatic control system where eventual modulated supply to the pneumatic interface 18.

Figure 34:
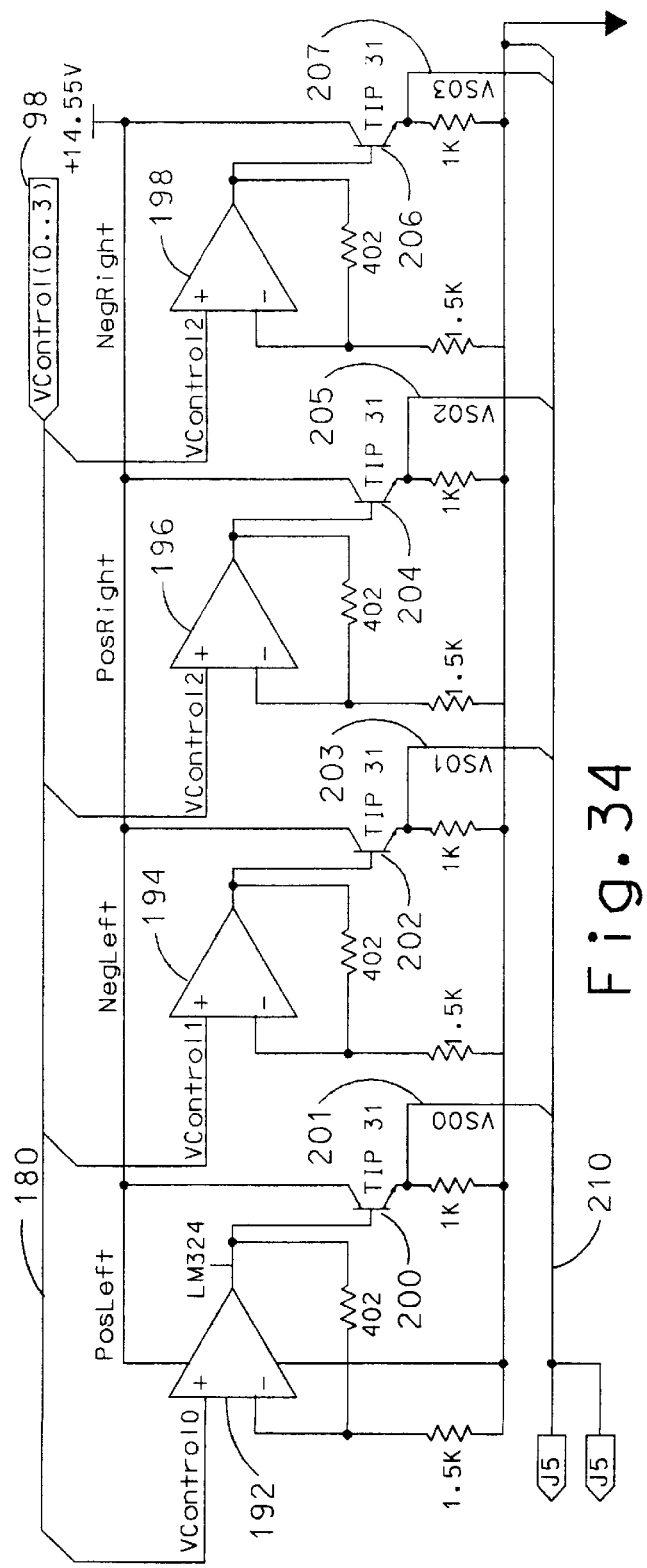
FIG. 34 is a schematic diagram of pressure proportioning electronics which, in response to valve error signals, provides proportional voltage valve control signals for controlling the analog flow proportional control valves.
Figure 35:
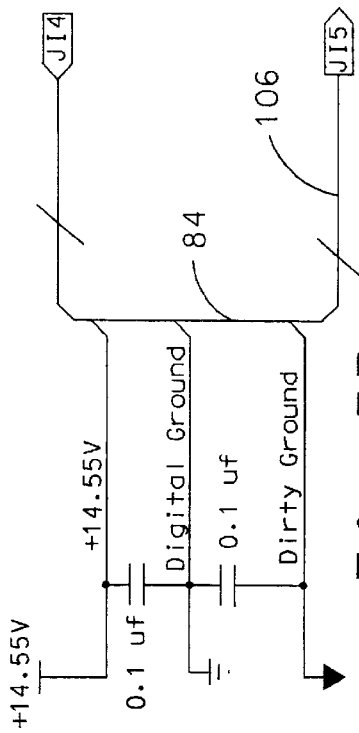
FIG. 35 is a schematic diagram of the power connections into the actuator board shown in FIG. 29.
Figure 36:
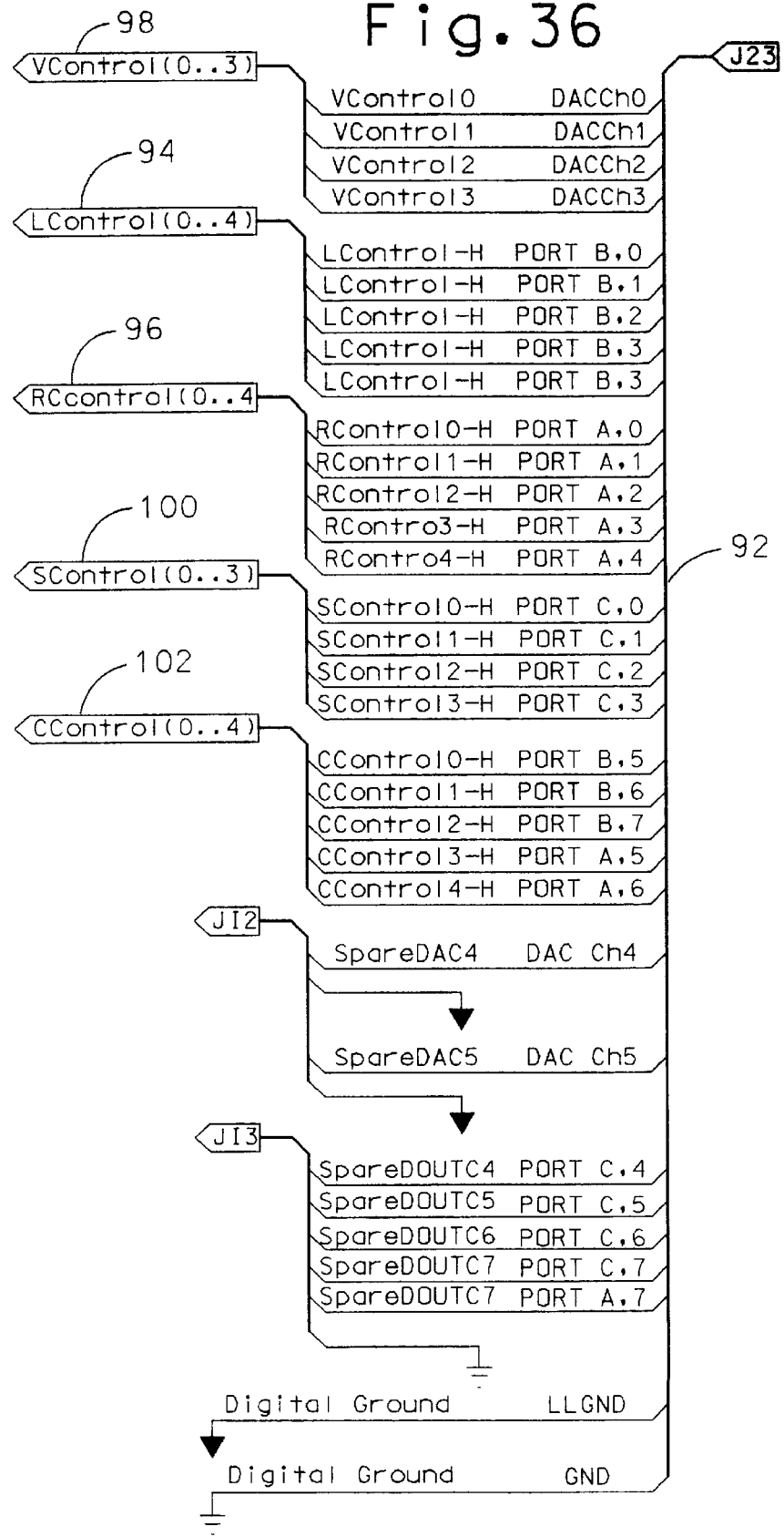
FIG. 36 is a schematic diagram of bus interconnections between an actuator board and a data acquisition board which interfaces with a computer.
Figure 44:
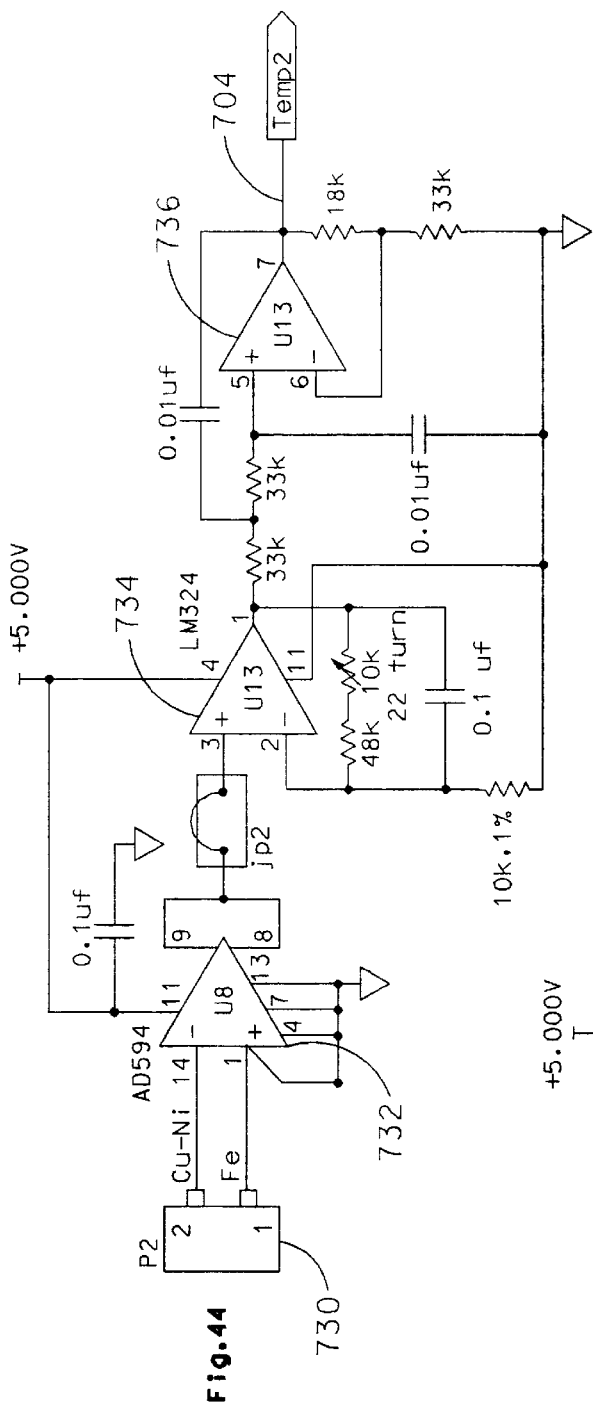

Valve command signals from the digital to analog card 90 are carried by the valve signal bus 92 to a pressure proportioning electronics module 180, as may best be seen in FIGS. 29, 36 and 34. More particularly, proportional valve command signals from the digital to analog card 90 are fed through the proportional valve control bus 98 to a plurality of valve drive amplifiers 190 are connected to a proportional flow valve bus 210. The plurality of valve drive amplifiers 190 comprise a positive left amplifier 192, a negative left amplifier 194, a positive right amplifier 196 and a negative right amplifier 198. The positive left amplifier 192 drives a power transistor 200. Likewise, the amplifiers 194, 196 and 198 drive respective power transistors 202, 204 and 206 which feed proportional flow valve drive signals via respective proportional flow valve control signal lines 201, 203, 205 and 207 comprising a portion of a proportional valve control bus 210 for supply to the plurality of analog valves 212 as may best be seen in FIG. 29. Each of the amplifiers functions as a linear amplifier having a gain of about 1.25 which provides a valve control signal to open each of the respective proportional flow valves connected to it by a predetermined amount. The pressure proportioning electronics 180 is energized with positive 14.55 volt signals from the power supply bus 84 as shown in FIG. 35.

The digital to analog conversion module 90 in response to signals from the computer 34 also controls a plurality of three way valves through digital valve control electronics as may best been seen in FIGS. 29 through 32. The left valve control bus, extending from the digital to analog converter card 90, feeds valve control signals through a ULN2003 driver to a plurality of direct valve control lines 220 coupled to a first plurality of the three-way valves. Likewise, the right valve control bus 96 feeds through a ULN2003 driver 104 to a right valve control bus 222 connected to the right on/off valves for controlling air flow to a second plurality of valve actuator openings in the pneumatic interface 18.

Figure 32:
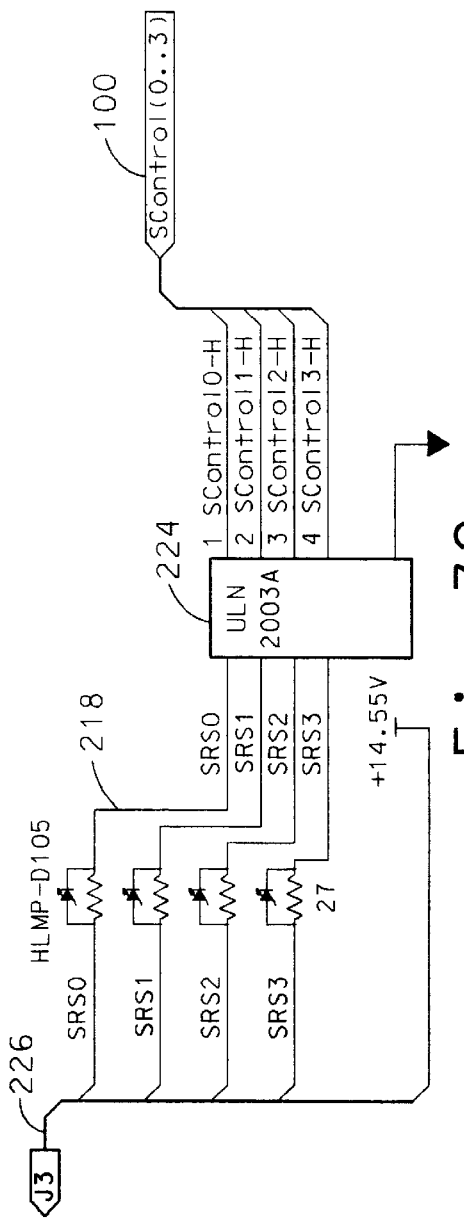
FIG. 32 is a schematic diagram of a control system for four large digital pneumatic valves.

As may best be seen in FIG. 32, the pneumatic routing control valve signals supplied by the bus 100 are fed to a ULN2003 driver 224 and to a routing valve control bus 226 to control the routing of high and low pressure air from the compressors and to other portions of the pneumatic system 16.

The compressors 178 comprise a first compressor 240 operated as a positive pressure pump and a second compressor 242 operated as a vacuum pump respectively connected to the AC control lines 174 and 176 to receive power therefrom and to be started up at the command of the computer 34. The compressor 178 supplies high pressure air at a pressure of plus 7.5 pounds per square inch gauge to a positive pressure line 244 for delivery to an eight valve manifold 246. The negative or vacuum system 242 draws a −7.5 psig vacuum on a vacuum line 248.

The pressure is delivered to a first pressure manifold line 250 for distribution within the eight valve manifold and via a check valve 252 to a second positive pressure line 254 for supply to other valves as well as two reservoirs and the like. The vacuum on line 248 is delivered to a first manifold vacuum line 258 and also to a second manifold vacuum line 260.

Figures 22, 23:
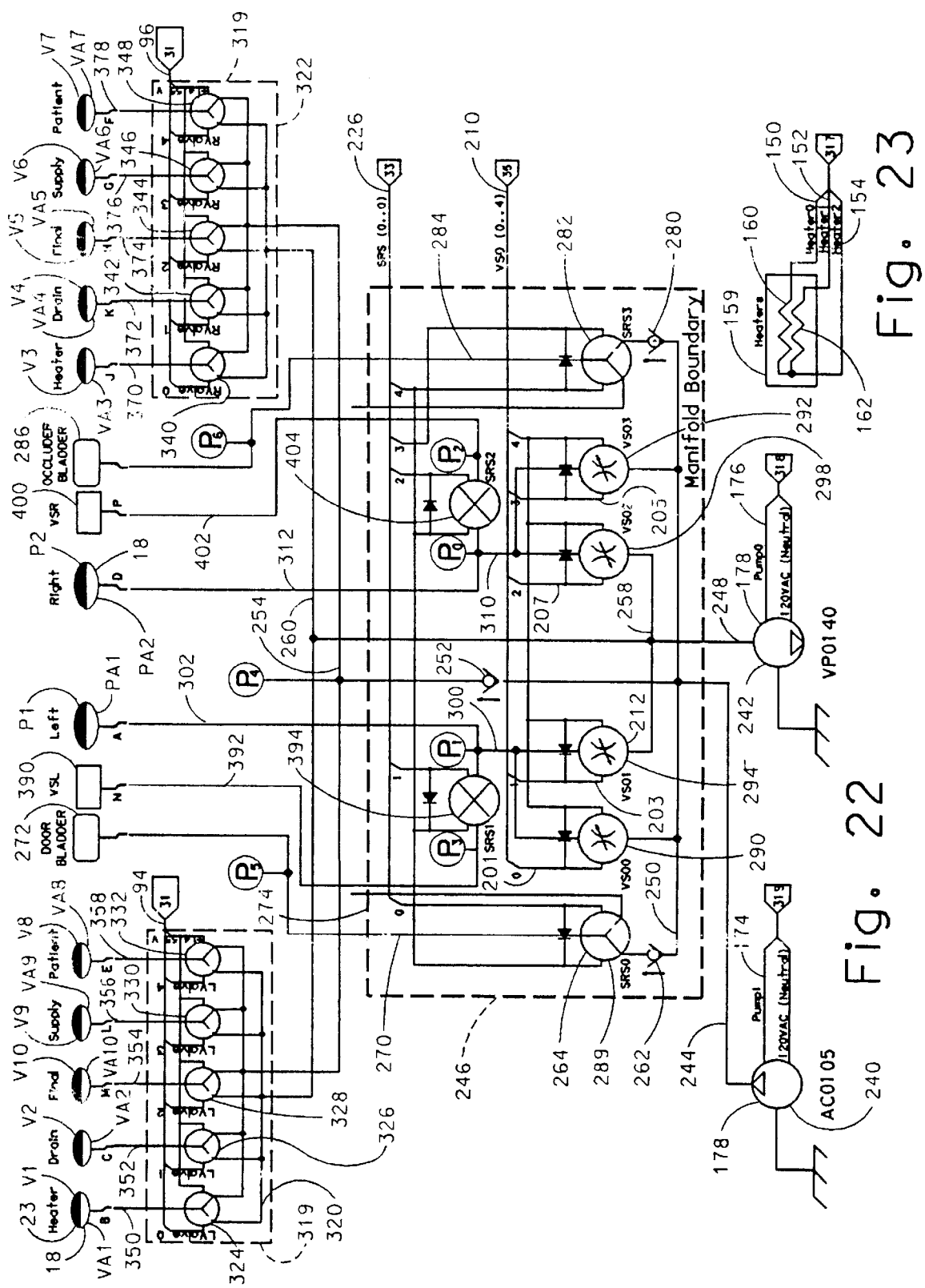
FIG. 22 is a schematic diagram of the pneumatic system of the APD system shown in FIG. 1.
FIG. 23 is a block diagram of a heater circuit for heating a dialysate bag.

The positive pressure is supplied from the manifold line 250 through a check valve 262 to a three-way valve 264 coupled to receive signals from one of the lines in the bus 226 shown in FIGS. 22 and 32.

The system communicates positive pressure via a high pressure line 270 to a door bladder 272 for holding the cassette 23 of liquid delivery set 21 in good interfacing contact with the pneumatic interface 18. A pressure transducer P5 is connected to the line 270 to measure the pressure thereon. A vent line is also provided coupled to the other portion of the door bladder valve 264.

Similarly, the positive pressure manifold 250 communicates through a check valve 280 to an occluder bladder valve 282 also driven from the bus 226 and in communication via an occluder pressure line 284 with an occluder bladder 286. The occluder bladder when deflated allows an occluder to crimp the flexible tubing of the liquid delivery set to block dialysate flow portions of the liquid delivery set to prevent flow of dialysate therefrom in the event of a power failure.

The ten valve manifold includes a left positive pressure proportional flow valve 290 coupled to the signal line 201 to be controlled by valve control signals thereon; and a right positive proportional pressure valve 292 connected to the signal line 205 by valve control signals thereon. Similarly, a left negative pressure proportional flow valve 294 is connected to the negative manifold 258 and controlled by signals on the line 203. A right negative pressure proportional flow valve 298 is controlled by signals on the line 207.

The left positive pressure and vacuum proportional flow valves 290 and 292 are connected via a line 300 to a pump pressure delivery line 302 in order to meter the air flow rate and the delivered pressure to the pneumatic interface 18 to control the pneumatic pressure delivered to one of the left diaphragm pump of the cassette 23. Likewise, since there are two diaphragm pumps available in the cassette, a left diaphragm pump and a right diaphragm pump, the valves 292 and 298 provide selected modulated pressure by a line 310 to a line 312 which is coupled to provide that pressure to the pneumatic interface 18 for delivery to the right diaphragm pump of the disposable dialysate cassette 23.

The use of one or more flow proportional valves 290, 292, 294, 298, see FIG. 22, in the pneumatic distribution system permits the modulation of pressure from compressor 240 or vacuum from vacuum pump 242 so that the desired level of pressure or vacuum may be transmitted to the pump actuators PA1 and PA2. The modulation of pressure or vacuum is desirable, e.g., for reasons of the patient's safety and comfort, such as to avoid sudden surges of dialysate being pumped into the patient's peritoneal cavity as might occur if raw pneumatic pressure were transmitted from a compressor to a pump actuator without modulation thereof. The flow proportional valves may be controlled to provide any of a number of predetermined pneumatic pressure versus time profiles, in order to ramp up or ramp down the pneumatic pump actuating pressure or vacuum, resulting in corresponding pressure versus time profiles for the pressure of the liquid dialysate being pumped from pumps P1 and P2. One may wish to use a ramp which is approximately linear or otherwise as may be desired. The flow proportional valves provide maximum flexibility for operation of the system 10 and, because they can modulate the raw pressure or vacuum communicated from the compressors, they eliminate the need for multiple reservoirs which might otherwise be needed to maintain certain discrete pressure levels.

Because it is unnecessary to modulate the air pressure supplied by the pneumatic interface 18 to liquid control valves within the cassette body, raw high pressure or vacuum are supplied respectively via the high pressure line 254 and the vacuum line 252 to a left three-way valve assembly 320 and a right three-way valve assembly 322. The left three-way valve assembly 320 controls the supply of pressure and vacuum to valve actuators in the pneumatic interface 18. It includes a heater pneumatic valve 324, a drain pneumatic valve 326, a final dialysate pneumatic bag valve 328, a dialysate supply pneumatic valve 330 and a patient pneumatic valve 332. Likewise, in right manifold 322 are a heater pneumatic valve 340, a drain pneumatic valve 342, a final dialysate pneumatic valve 344, a supply pneumatic valve 346 and a patient dialysate pneumatic valve 348. The pneumatic valves of the assemblies 320 and 322 are pneumatically connected to the pneumatic peripheral interface 18 via a plurality of flexible supply tubes 349. The plurality of flexible supply tubes 349 includes a heater supply tube 350 connected to the valve 324, a drain supply tube 352 connected to the valve 326, a final supply tube 354 connected to the valve 328, a bag or dialysate supply tube 356 connected to the valve 330 and a patient supply tube 358 connected to the valve 332.

The heater supply tube 350 is connected to a valve actuator VA1. A line 352 is connected to a valve actuator VA2. For the right hand portion of the cassette 23 a heater line 360 is connected to the valve 340, a drain line 372 is connected to the valve 342, a final dialysate bag line 374 is connected to the valve 344, a supply or dialysate bag line 376 is connected to the valve 346 and a patient line 378 is connected to the valve 348.

A valve actuator VA3 is connected to the heater line 370, a valve actuator VA4 is connected to the drain line 372, a valve actuator VA5 is connected to the final supply line 374, a valve actuator VA6 is connected to the line 376, a valve actuator VA7 is connected to the line 378, a valve actuator VA8 is connected to the patient's supply line 358, a valve actuator VA9 is connected to the patient's supply line 356 and valve actuator VA10 is connected to the patient's supply line VA10.

As stated previously herein, the use of flow proportional valves 290, 292, 294, 298, as shown in FIG. 22, for modulation of pneumatic pressure and for obtaining pressure versus time profiles makes it possible to avoid the use of multiple pneumatic reservoirs which might otherwise be needed for supply of specific pneumatic pressure levels. The elimination of reservoirs, in turn, permits a reduced number of pneumatic valves which would be needed for communication with such reservoirs if used in the pressure distribution system. A reduced number of pneumatic valves, made possible by the invention, may be observed in FIG. 22. While the pump actuators PA1 and PA2 receive modulated pneumatic pressure or vacuum from the flow proportional valves, in order to modulate the pressure and the flow of liquid dialysate being pumped by pumps P1 and P2, it is preferable for the valve actuators VA1–10 to receive a predetermined magnitude of pressure or vacuum, without modulation by pneumatic flow proportional valves, in order to ensure that the liquid valves V1–10 are either fully open or fully closed, or moving relatively quickly from one position to the other.

A left standardized volumetric reservoir 390 is connected via a line 392 to a valve 394 which is in communication with a line 302 and is controlled by the bus 226. A pressure transducer PT3 is connected to the line 392 and the pressure transducer PT1 is connected to the line 302. The valve 394 in combination with the pressure transducers PT1 and PT3 and the volumetric reservoir 390 is used to measure absolute pressure and pumping characteristics and the like associated with the left diaphragm pump of the cassette.

Likewise, a right standardized volumetric reservoir 400 is connected via a pneumatic line 402 to receive high pressure air from a valve 404 connected to the bus 226. Pressure transducers PT0 and PT2 are respectively connected to the pneumatic lines 312 and 402 so that the valve 404 from time to time can connect the right pressure actuator to the standardized volumetric reservoir and measure pressures before and after such connection and supply the pressure transducer signals thereto. The pressure transducer PT6 is connected to the line 284 to provide signaling to the microprocessor 34 as to the condition of the occluder bladder. The pressure transducer P4 is connected to the positive pressure line and the pressure transducer PT5 is connected to the door bladder line 270.

In operation a door assembly 450, including a door 452, which is hingedly mounted on the housing 32, is adapted to hold and engage a portion of the liquid delivery set within the door assembly 450 in good pneumatic engagement with the pneumatic interface 18, as may best be seen in FIGS. 1 and 12 through 15. The door assembly 450 includes a front plate 454 comprising a portion of a cassette holder, the front plate 454 being generally rectangular and having a substantially rectangular cassette receiving aperture 456 formed therein. The cassette receiving aperture 456 is a portion of a cassette receiving interior recess 458 which extends into a backplate 460. The backplate 460 also includes a slot 462 through which a portion of an occluder assembly may extend. Extending from a front face 461 of the backplate 458 is a latch pin 466 for locking engagement with the door 452 in order to hold the door 452 securely while the cassette 23 is within the door assembly 450. A resilient foam spring element 470, having a substantially rectangular window 472 defined therein, sits against the backplate 470 and has a preformed gasket 480 mounted on a side opposite the latch pin 466 for holding the cassette 23 in good pneumatic engagement with the pneumatic interface 18. The preformed gasket 480 includes an integral elastomeric splash guard membrane 482 for preventing any leaking dialysate from entering the pneumatic interface 18 and a plurality of small air transmitting through holes 484 are formed therein for pneumatic communication with the flexible tubes coupling the valve actuators VA1–10 and pumps P1 and P2 with other portions of the pneumatic system and other ports of the pneumatic interface 18. A pair of foam inserts are positioned behind the gasket 480 in association with the pump actuators PA1 and PA2 of the pneumatic interface 18 to smooth pressure transfer from the pneumatic interface 18 to the cassette 23.

The cassette holder module also includes a substantially rectangular pressure plate 500, having the door bladder 272 positioned behind it. A frame for holding the door bladder 272 is positioned on the opposite side of the door bladder and the occluder bladder 286 is positioned on the other side of the frame 502. A movable occluder body 504 is positioned on a side of the occluder bladder 286 opposite the frame 142 so that the occluder bladder 286 is positioned therebetween. When the occluder bladder 286 is inflated an elongated occluder blade 506 will be lifted away from other portions of the frame 502. An elongated side hook element 508 is provided on the opposite side of the movable occluder body 504 to provide a pivot about which the entire body 504 moves under the influence of the occluder bladder 286 and a pair of occluder springs 510 coupled to a pair of sleeves 512 mounted in association with the movable occluder body 504.

Figure 10:
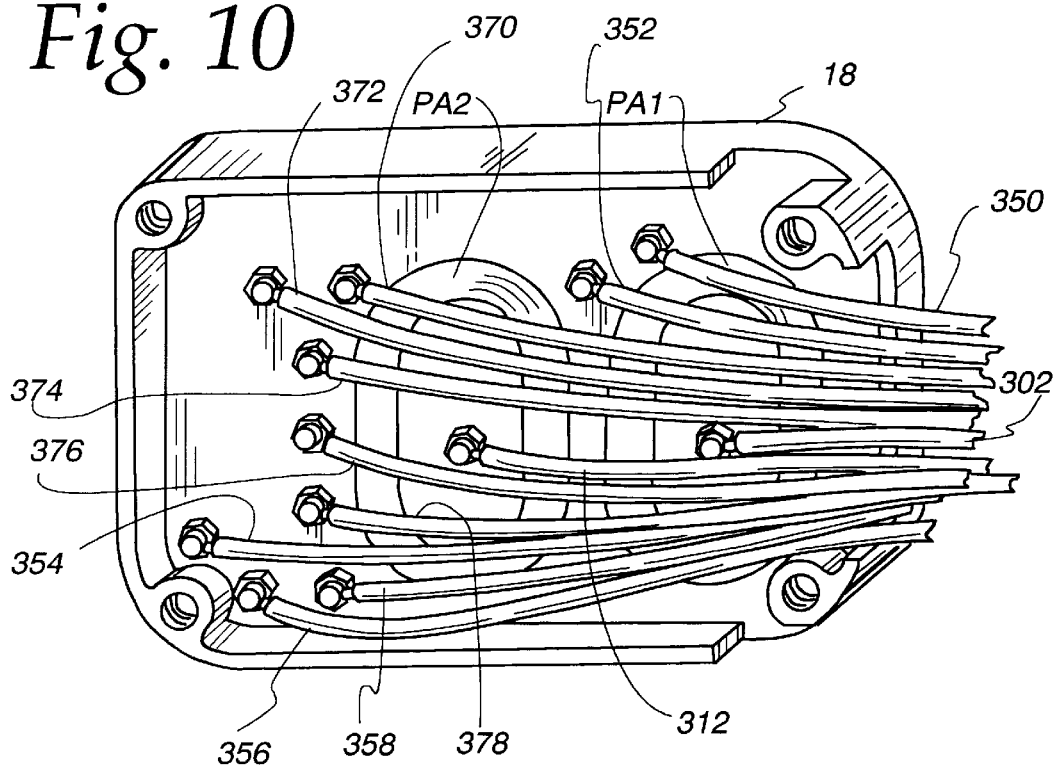
FIG. 10 is a rear elevational view of the pneumatic interface shown in FIG. 9.
Figure 11:
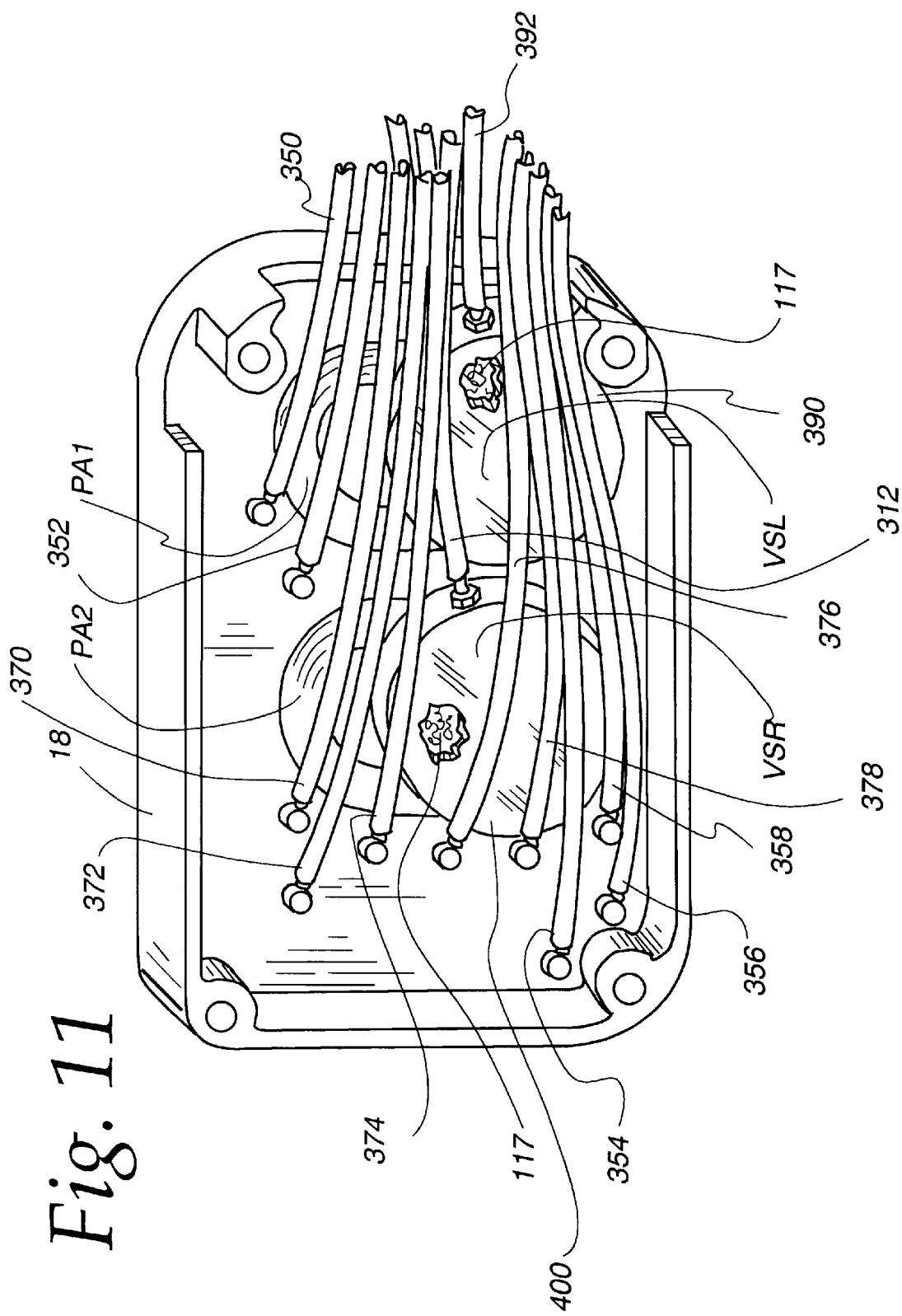
FIG. 11 is a rear elevational view of the pneumatic interface shown in FIG. 9 showing details of volumetric pneumatic measuring chambers thereon.
Figure 12:
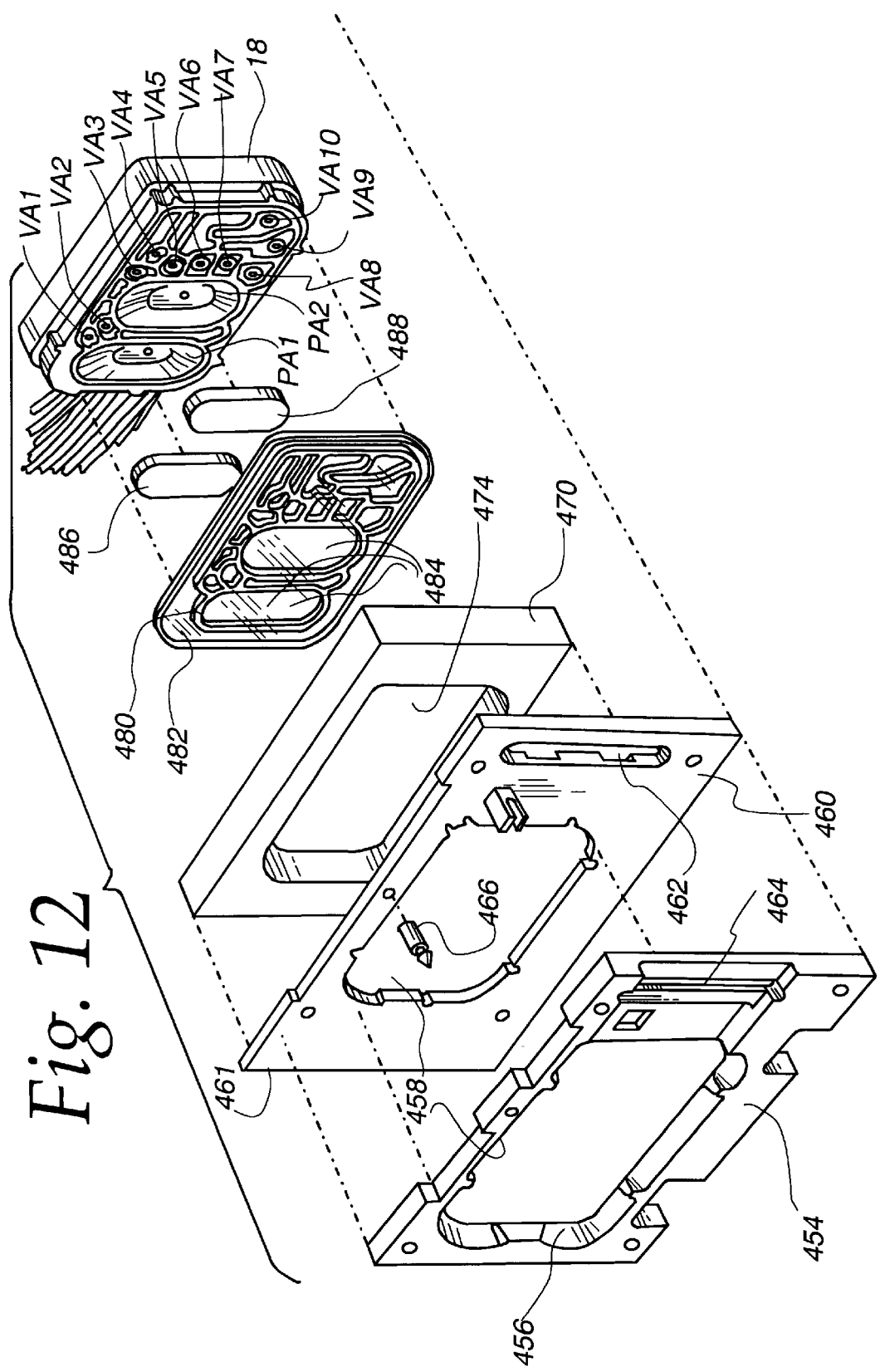
FIG. 12 is an exploded perspective view of the pneumatic interface and the disposable cassette with other portions of a door assembly of the cycler shown in FIG. 1.
Figure 13:
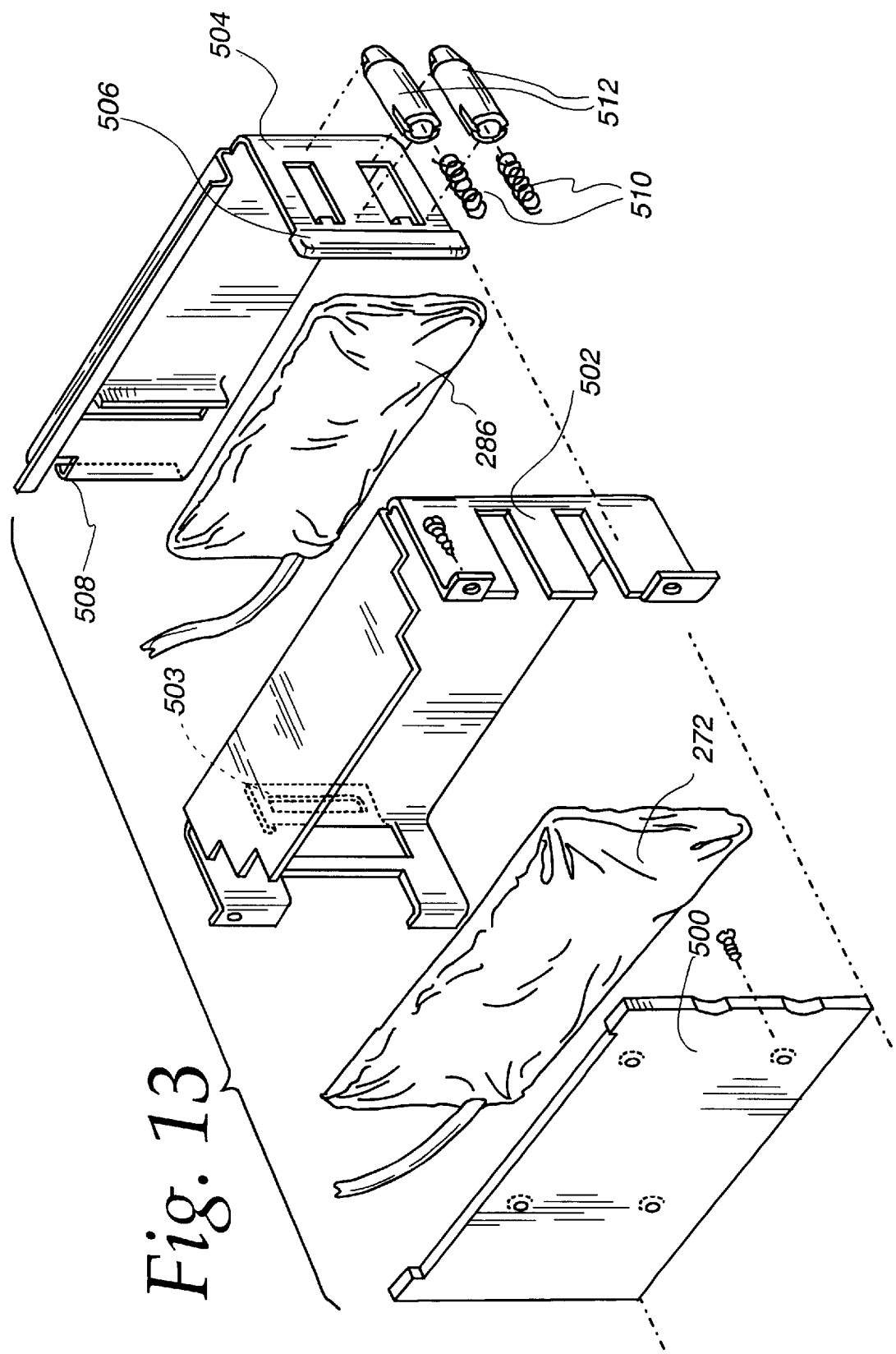
FIG. 13 is an exploded perspective view of portions of the door assembly shown in FIG. 12 with details of a door bladder and an occluder bladder shown therein.
Figure 14:
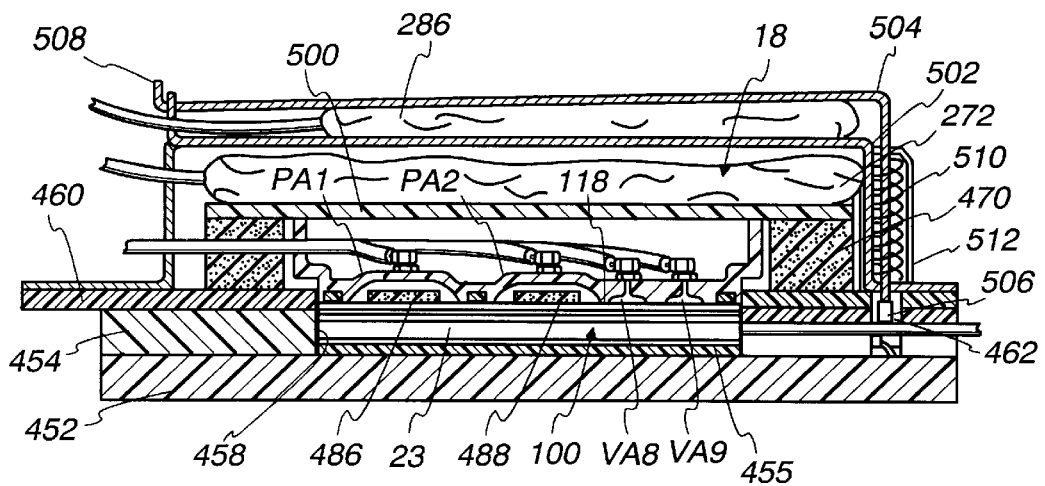
FIG. 14 is a sectional view of the door assembly in an engaged position with the door bladder deflated.
Figure 15:
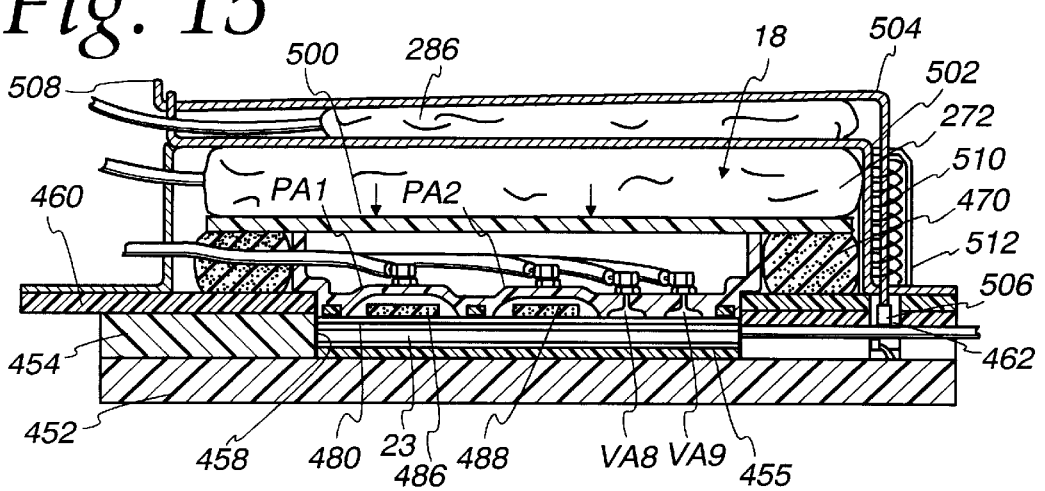
FIG. 15 is a sectional view of the door assembly shown in FIG. 14 with the door bladder inflated.
Figure 16:
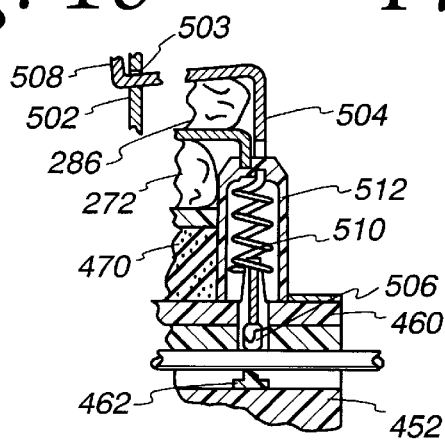
FIG. 16 is a sectional view of a portion of the door assembly showing details of the action of the occluder bladder when inflated allowing dialysate flow through the disposable dialysate delivery set.
Figure 17:
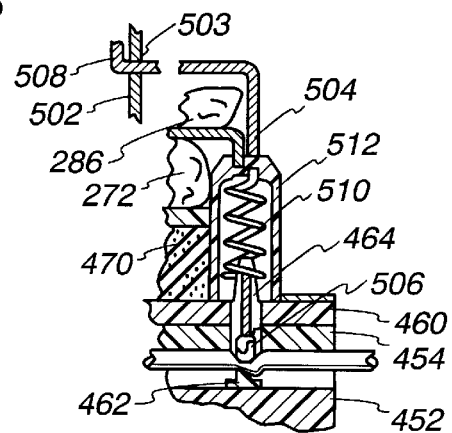
FIG. 17 is a sectional view of the portion of the door assembly shown in FIG. 17 with the occluder bladder deflated and the occluder blocking dialysate flow in the disposable dialysate delivery set.
Figure 18:
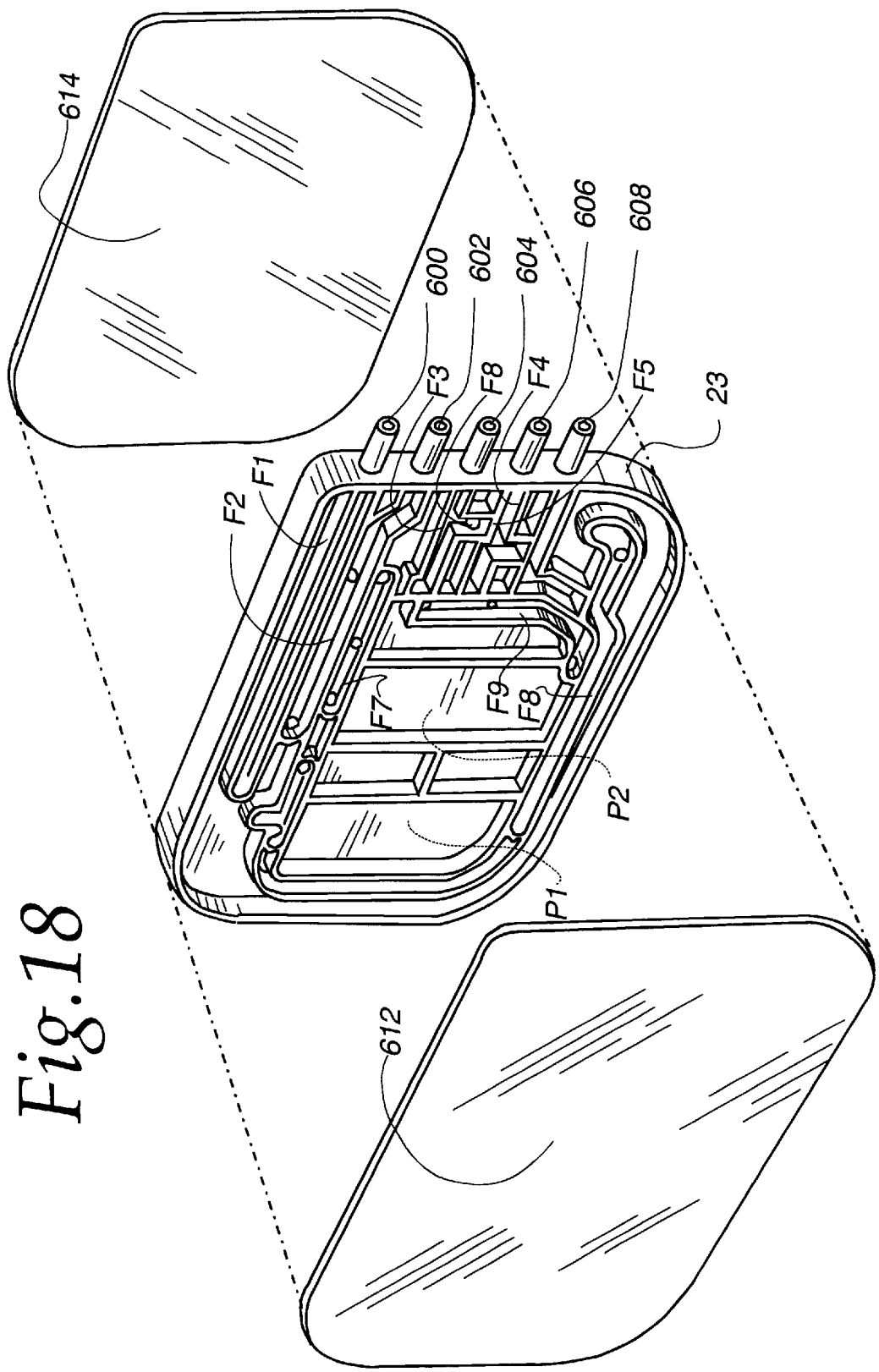
FIG. 18 is an exploded perspective view of a disposable dialysate cassette.

As may best be seen in FIG. 11 an alternative pneumatic interface 18 is shown therein which is substantially identical to the pneumatic interface shown in FIG. 10 with the exception that pressure measuring volumes VSR and VSL are attached to the back of the pneumatic interface 18 and are each filled with a heat conductive foam insert 117. The heat conductor foam insert provides heat transfer which smoothes pressure variations as the profile pressure is supplied along lines 312 and 392 via the flow proportioning valves. The helps to reduce pressure spikes at the patient which may prove to be uncomfortable.

Figure 21:
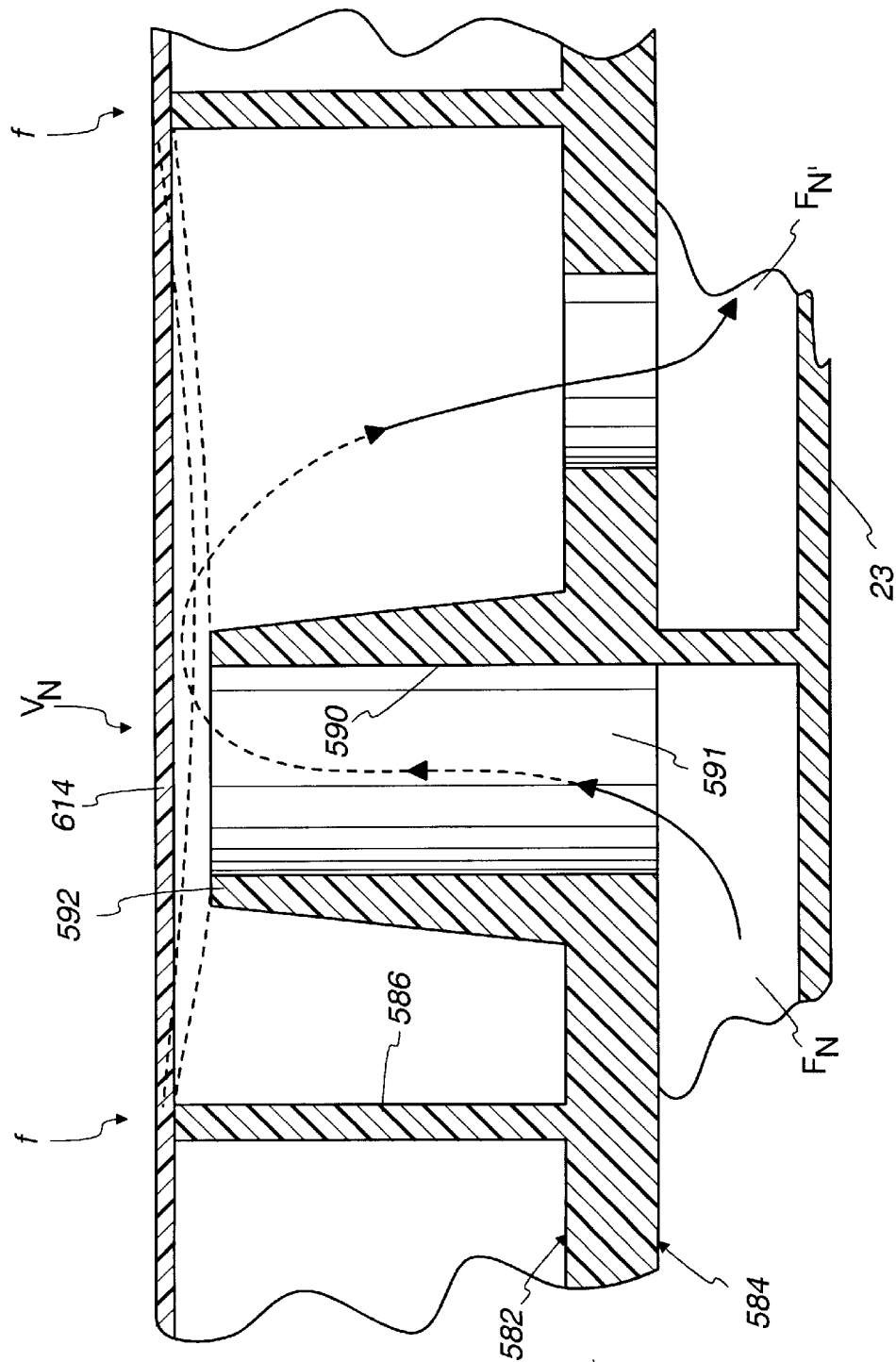
FIG. 21 is an enlarged sectional view of a portion of the disposable dialysate cassette shown in FIG. 18 showing details of a dialysate valve.

As shown in FIG. 21, the cassette body 23 includes a front side 582 and a back side 584. A plurality of upstanding ribs 586 support the diaphragm 614 which may be brought into sealing engagement with a hollow column 590 which defines a port 591 at a raised valve seat 592. When the diaphragm is in communication with the upper portion of the column the fluid in the column will not be in communication with a second port 594.

Figure 19:
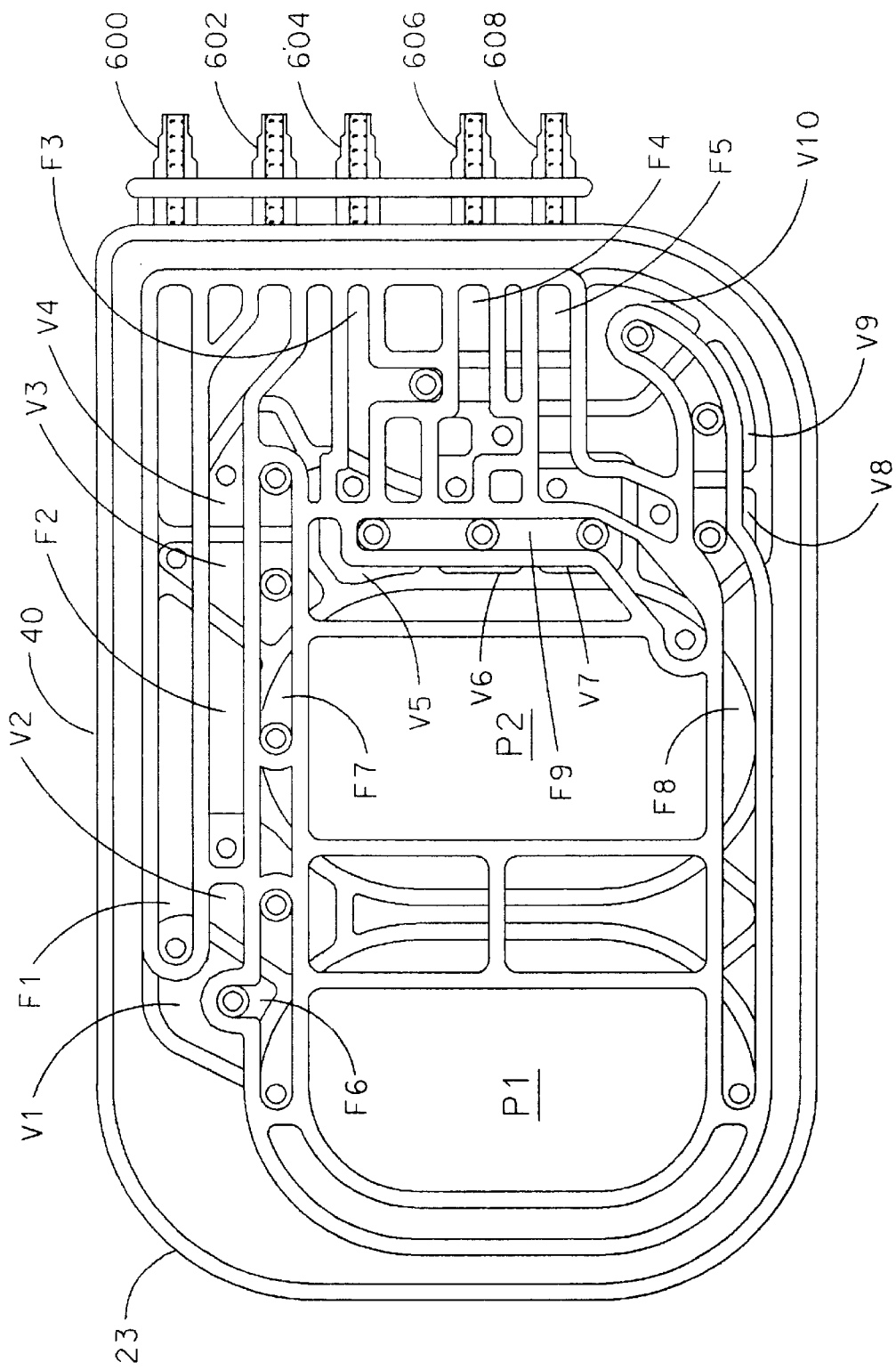
FIG. 19 is an elevational view of one side of a body of the disposable dialysate cassette shown in FIG. 18.
Figure 20:
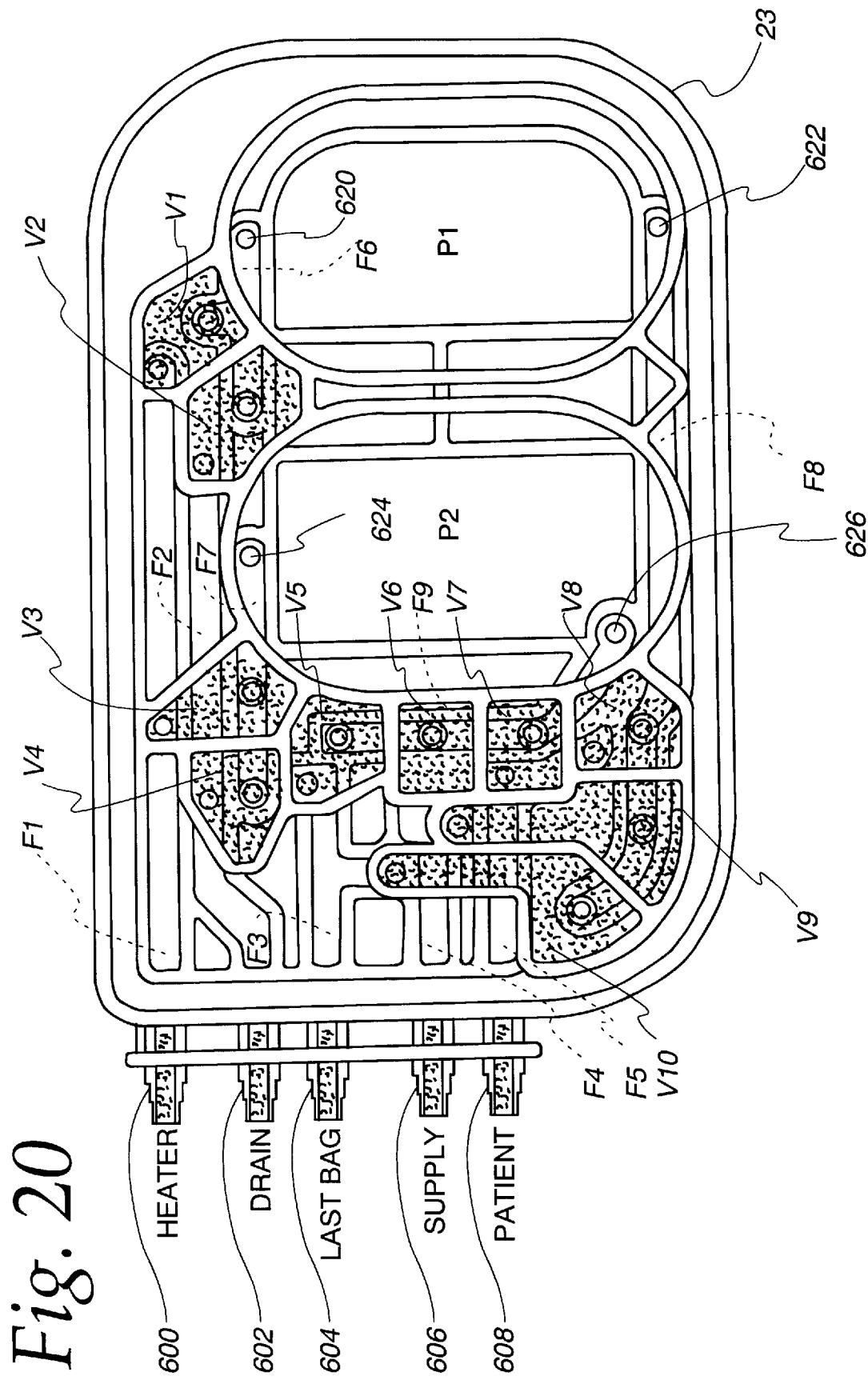
FIG. 20 is an elevational view of the opposite side of the body of the disposable dialysate cassette shown in FIG. 19.

In use, the cassette 23 of the dialysate delivery set 21 is placed in the cassette holder in such a way that the plurality of flexible tubes past the occluder. The cassette 21, as may best be seen in FIGS. 19, 20 and 21, includes the cassette body 23 terminating at five dialysate ports on a side thereof. They include a heater bag port 600, a drain port 602, a last dialysate bag port 604, a supply bag or dialysate supply port 606 and a patient port 608. Formed within the cassette body are a plurality of channels, some of which are connected to the ports. Also included therein are a pair of pump chambers P1 and P2. The pump chambers and the channels are enclosed by the pair of flexible plastic diaphragms 612 and 614.

The heater bag port 600 has connected to it a heater bag channel F1. The drain port 602 has connected to it a drain channel F2. The last bag port 604 has connected to it a last bag channel F3. The supply port 606 has connected to it a dialysate supply channel 504 and the patient port 608 has connected to it a patient dialysate channel F5. The pump chamber V1 includes an upper pump chamber port 620 and a lower pump chamber port 622. The pump chamber P2 includes an upper pump chamber port 624 and a lower pump chamber port 626. The upper pump chamber port 620 of pump chamber P1 may be coupled to the heater bag channel F1 or the drain channel F2 via a P1 upper distribution channel F6. The upper port 624 of the pump chamber P2 may be coupled to the heater bag channel F1 or the drain channel F2 via a upper pump chamber P2 distribution channel F7.

In a similar fashion, the pump chamber Pi lower port 622 may be coupled to the last bag channel F3, the supply channel F4 or the patient channel F5 via a lower P1 pump channel F8. The lower port 626 of the pump chamber P2 may be coupled to the last bag channel F3, the supply channel F4 or the patient channel F5 via a lower P2 distribution channel F9.

Ten valve stations are provided for effecting the coupling between the main dialysate channels F1 through F5 and the pump chamber distribution channels F6 through F9. Specifically, a valve station V1 couples the heater bag line F1 to the pump channel F6. A valve V2 couples the drain channel F2 to the upper P1 distribution channel F6. The valve station V3 couples the heater bag channel F1 to the upper P2 distribution channel F7. A valve station V4 couples the drain channel F2 to the upper pump P2 distribution channel F7.

A valve V5 couples the last bag channel F3 to the lower pump chamber P2 channel F9. A valve V6 couples the supply channel F4 to the lower pump chamber P2 distribution channel F9. A valve V7 couples the patient channel F5 to the lower pump chamber P2 distribution channel F9.

A valve V8 couples the patient channel F5 to the lower pump chamber P1 channel F8. A valve V9 couples the supply bag channel F4 to the lower pump chamber P1 distribution channel F8. A valve V10 couples the last bag supply channel F3 to the lower pump chamber P1 distribution channel F8.

When the valves V1 through V10 are opened due to low pressure being applied through the pneumatic interface to regions of the valves where the diaphragm is seated, the valves are opened and the aforementioned selected flow connections are made. When high pressure is supplied via the local valve actuators VA1 through VA10 to the respective valve stations V1 through V10 of the cassette, the valves are held closed. Thus, manipulation of the pressures at the valve actuators VA1 through VA10 by the valves in the manifolds 320 and 322 controls the manner in which dialysate is distributed between the ports 600 through 608 and the pump chambers P1 and P2.

At the same time pressure is supplied via the flow proportional valves to the pump actuators PA1 and PA2 of the pump chambers to move the diaphragm portions adjacent those chambers to cause pumping to occur.

The cassette, when delivering dialysate to and from the patient and to various bags, sometimes access dialysate from the heater bag 22 which is heated by the heaters 159. A thermocouple assembly 700, as may best be seen in FIGS. 29 and 42 through 47, supplies temperature signals indicative of the heating bag temperature. The signals temp0 through temp5 are supplied from thermocouple conditioning electronics 702 over an analog temperature signal bus 704 to an analog to digital conversion card 706, specifically a Keithley-Metralyc DAS1402 analog input card. The analog input card 706 in turn transfers digital temperature signals over the bus 36 to the computer 34 where the computer 34 can adjust the control inputs to be received by the heater power electronics 118.

Figure 45:
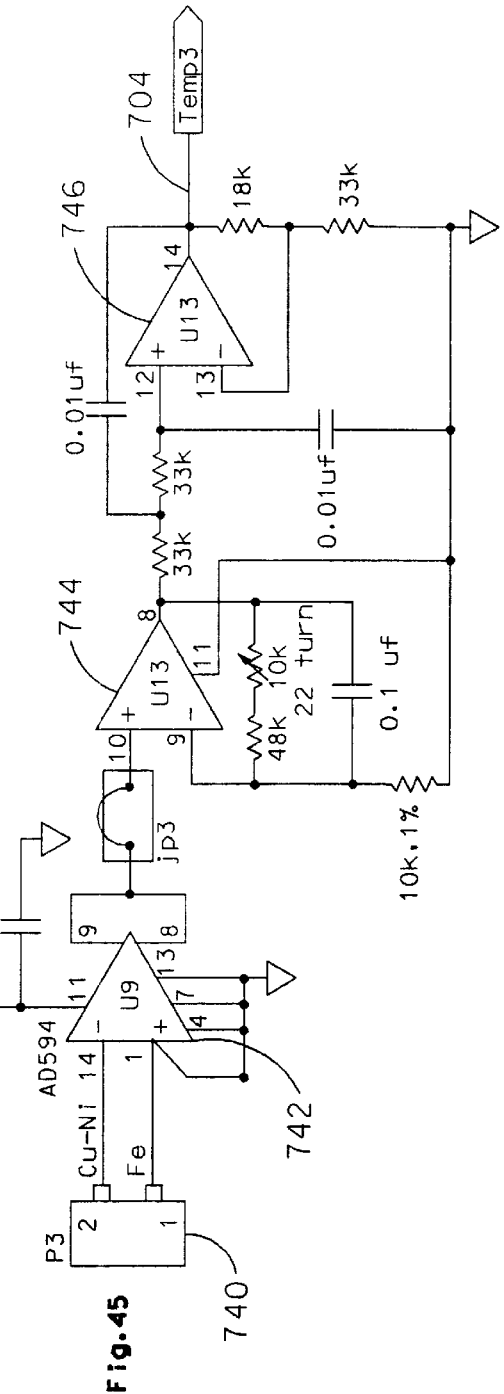

More specifically, each of the circuits in FIGS. 42 through 47 is identical and includes a thermocouple 710 coupled to an amplifier 712 feeding an amplified output signal across a jumper 714 to a second amplifier 716 and finally to a third stage amplifier 718, which provides an output signal. Likewise, as shown in FIG. 43 a thermocouple 720 has its signal amplified by a first amplifier 722, a second amplifier 724 and a third amplifier 726. A thermocouple 730 has its output signal amplified by amplifiers 732, 734 and 736 and supplied to the bus 704. As shown in FIG. 45 a thermocouple 740 has its signal amplified by amplifiers 742, 744 and 746 and supplied to the bus 704. As shown in FIG. 46, a fifth thermocouple 750 has its output signal amplified by amplifiers 752, 754 and 756 and supplied to the bus 704. A sixth thermocouple 760, as shown in FIG. 47, has its output amplified by amplifiers 762, 764 and 766 and supplied to the analog bus 704.

Figure 53:
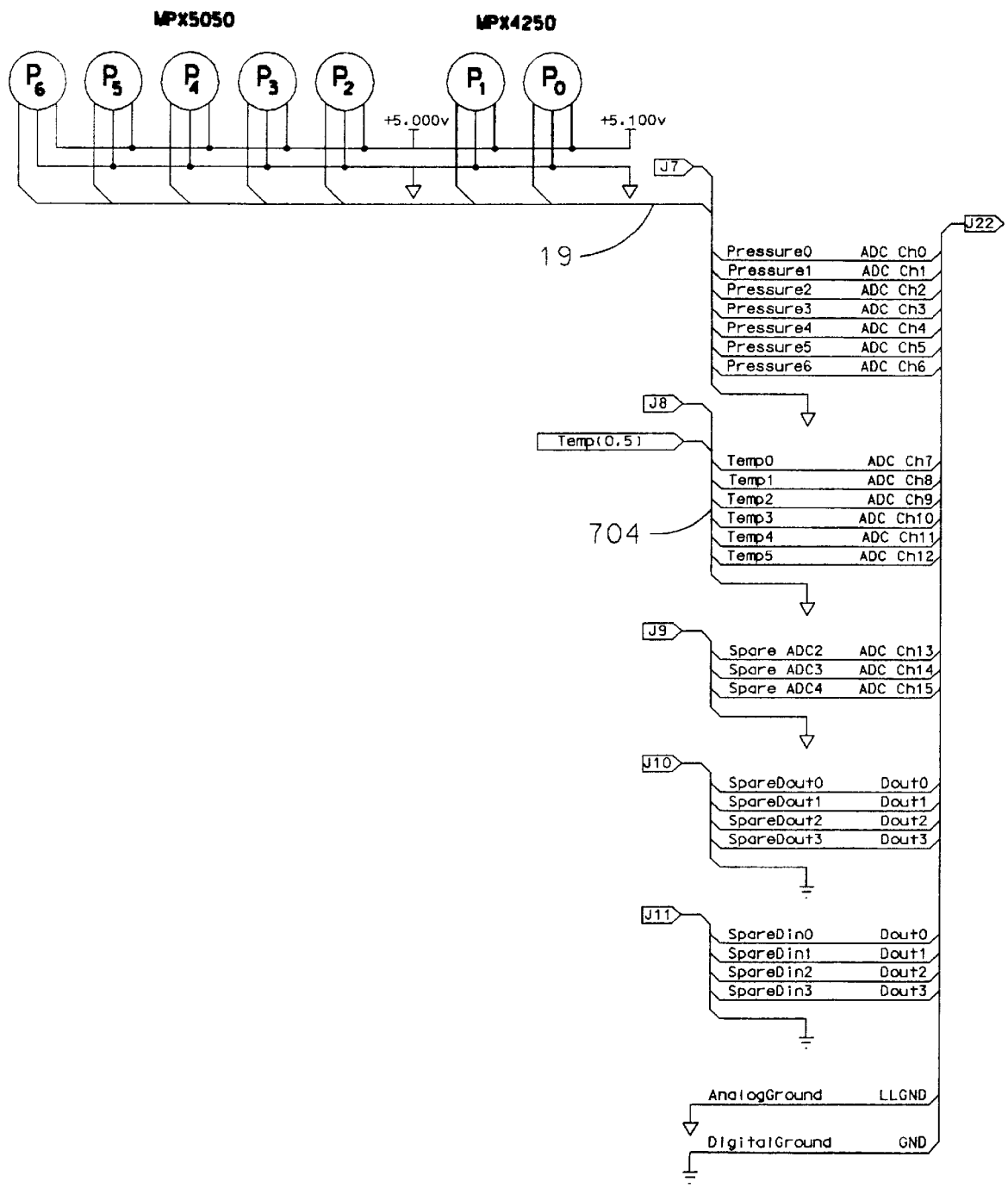

In a similar fashion, the output of the pressure transducers is supplied over the feedback bus 19 to the analog to digital card 706 as shown in FIGS. 29 and 53. The pressure signals are digitized and fed to the computer 34 where the computer 34 can then monitor the pressures of the bladders, monitor the flow rates and also control the analog valves or flow proportional valves 212 in order to select the delivered pressures to be provided to the pump actuators PA1 and PA2 and hence the pressure at the dialysate in the pump chambers P1 and P2 of the cassette 23.

In the fill phase of the typical three phase APD cycle the cycler 14 transfers dialysate from the heater bag 22 to the patient. The heater bag 22 is attached to the uppermost cassette port. The patient line is attached to the bottommost cassette port. The fill phase involves drawing dialysate into the cassette pump chamber P1 through the primary liquid path F1 via branch liquid path F6. Then pump chamber P1 expels the heated dialysate through the primary liquid path F5 via branch liquid path F8.

To expedite pumping operations, the cycler 14 preferably works pump chamber P2 in tandem with pump chamber P1. The controller 14 draws heated dialysate into pump chamber P2 through primary liquid path F1 via branch liquid path F7.

Then, the pump chamber P2 expels the heated dialysate through the primary liquid path F5 through branch liquid path F9. The controller 14 works pump chamber P1 in a draw stroke, while working pump chamber P2 in a pump stroke, and vice versa.

In this sequence heated dialysate is always introduced into the top portions of the pump chambers P1 and P2. The heated dialysate is always discharged through the bottom portions of the pump chambers P1 and P2 to the patient free of air.

Furthermore, during liquid transfer directly with the patient the controller 14 can supply only low-relative positive and negative pressures to the pump actuators PA1 and PA2.

Once the programmed fill volume has been transferred to the patient the cycler 12 enters the second or dwell phase. During the dwell phase the cycler 12 replenishes the heater bag by transferring fresh dialysate from one of the source dialysate bags 22 to it.

The replenish heater bag phase involves drawing fresh dialysate into the cassette pump chamber P1 through the primary liquid path F4 via the branch liquid path F8. Then the pump chamber P1 expels the dialysate through the primary liquid path F1 via the branch liquid path F6.

To expedite pumping operations the controller 14 preferably works the pump chamber P2 in tandem with the pump chamber P1. The cycler 12 draws fresh dialysate into the cassette pump chamber P2 through the primary liquid path F4 via the branch liquid path F9. Then the pump chamber P2 expels the dialysate through the primary liquid path F1 via the branch liquid path F7.

The cycler 12 works the pump chamber P1 in a draw-stroke while working the pump chamber P2 in a pump stroke and vice versa.

During this sequence fresh dialysate is always introduced into the bottom portions of the pump chambers P1 and P2. The fresh dialysate is always discharged through the top portions of the pump chambers P1 and P2 to the heater bag. This allows entrapped air to be removed from the pump chambers P1 and P2.

Since liquid transfer does not occur directly with the patient, the controller 14 is able to supply high relative positive and negative pressures to the pump actuators PA1 and PA2 without directly affecting the patient.

When the dwell phase ends the cycler 12 enters a third or drain phase. During the drain phase the cycler 12 transfers spent dialysate from the patient 28 to a drain. The drain phase involves drawing spent dialysate into the cassette pump chamber P1 through the primary liquid path F5 via liquid branch F8. Then the pump chamber P1 expels the dialysate through the primary liquid path F2 via the branch liquid path F6.

In order to expedite pumping operations the controller works the pump chamber P2 in tandem with the pump chamber P1. The cycler 12 draws spent dialysate into the cassette pump chamber P2 through the primary liquid path F5 via the branch liquid path F9. Then the pump chamber P2 expels the dialysate through the primary liquid path F2 via the branch liquid path F7.

The cycler 12 senses pressure using transducers PT1 and PT2 to determine when the patient's peritoneal cavity is empty. Drain phase is followed by another fill phase and dwell phase as previously described.

In some APD procedures after the last prescribed fill/dwell/drain cycle, the cycler infuses a final fill volume. The final fill volume dwells in the patient through the day. It is drained at the outset of the next CCPD session in the evening. Final fill volume can contain a different concentration of dextrose than the fill volume of the successive CCPD fill/dwell/drain fill cycles the cycler provides. The chosen dextrose concentration sustains ultrafiltration of water during the day long dwell cycle.

In this phase the cycler infuses fresh dialysate to the patient from a last fill bag. The last fill bag is attached to the third cassette port.

During the last dwell phase the heater bag is emptied in solution from the last bag's volume transferred to the heater bag. From there, the last fill solution is transferred to the patient to complete the last fill phase.

The last dwell phase involves drawing liquid from the heater bag into pump chamber P1 through the primary liquid path F1 via the branch path F6. Pump chamber P1 expels the liquid to the drain through the primary liquid path F2 via the branch liquid path F6.

To expedite drainage of the heater bag the cycler 12 works the pump chamber P2 in tandem with the pump chamber P1. The cycler 12 draws liquid from the heater bag into the pump chamber P2 through the primary liquid path F1 via the branch liquid path F7. Then, the pump chamber P2 expels liquid to the drain through the primary liquid path F2 via the branch liquid path F7.

Once the last fill solution has been heated it is transferred to the patient in a fill cycle as set forth above.

According to one aspect of the invention, every important aspect of the APD procedure is controlled by air pressure. Air pressure moves liquid through the delivery set, emulating gravity flow conditions based upon either fixed or variable head height conditions. Air pressure controls the operation of the valves that direct liquid among the multiple destinations and sources. Air pressure serves to seal the cassette within the actuator and provide a fail safe occlusion of the associated tubing when conditions warrant. Air pressure is the basis from which dialysate volume measurements are made from which air entrapped in the liquid is detected and eliminated, and from which occluded liquid flow conditions are detected and diagnosed.

Figure 54:
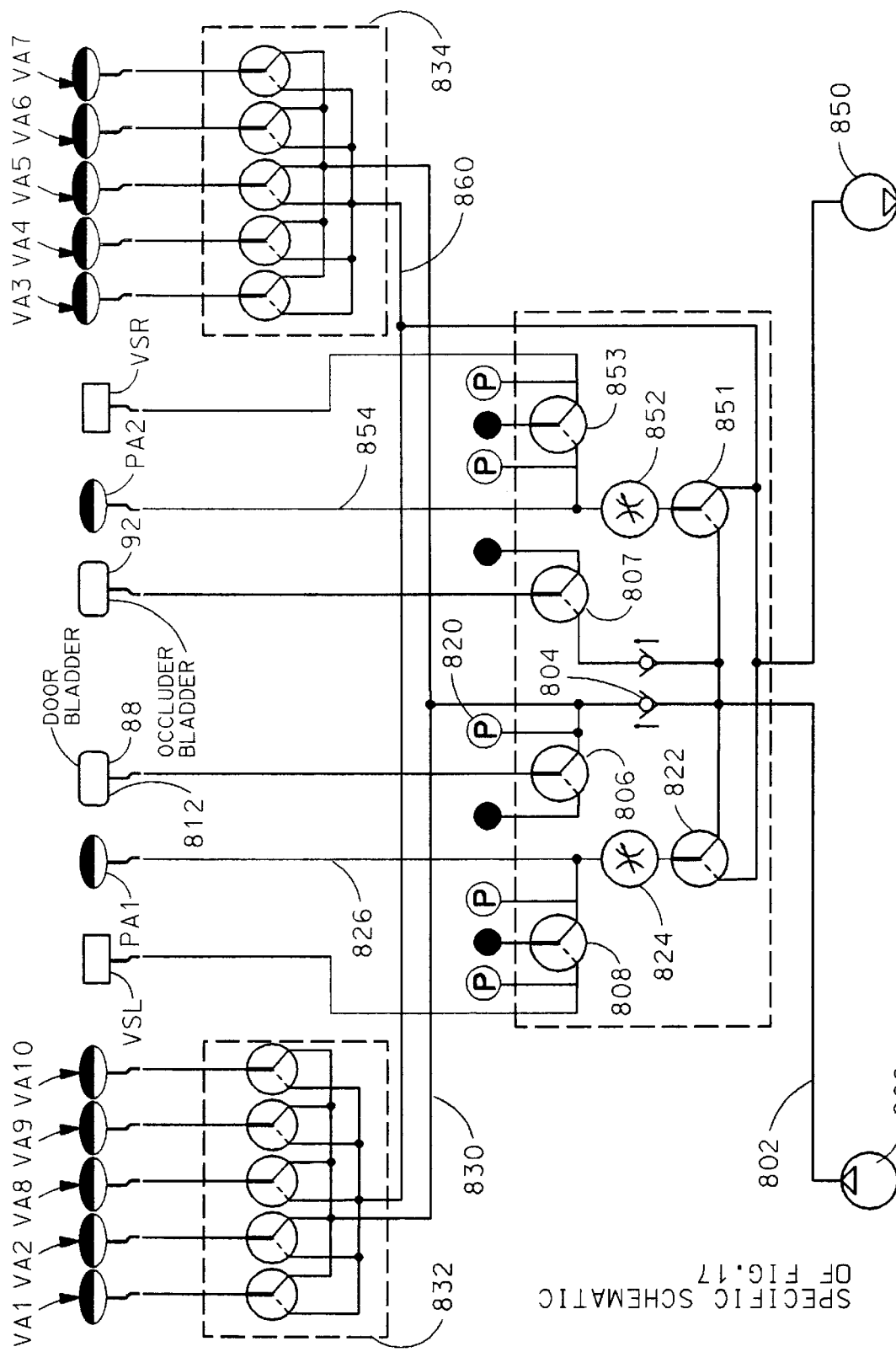
FIG. 54 is a schematic diagram of the second embodiment of a pneumatic system of the APD system shown in FIG. 1.
Figure 55:
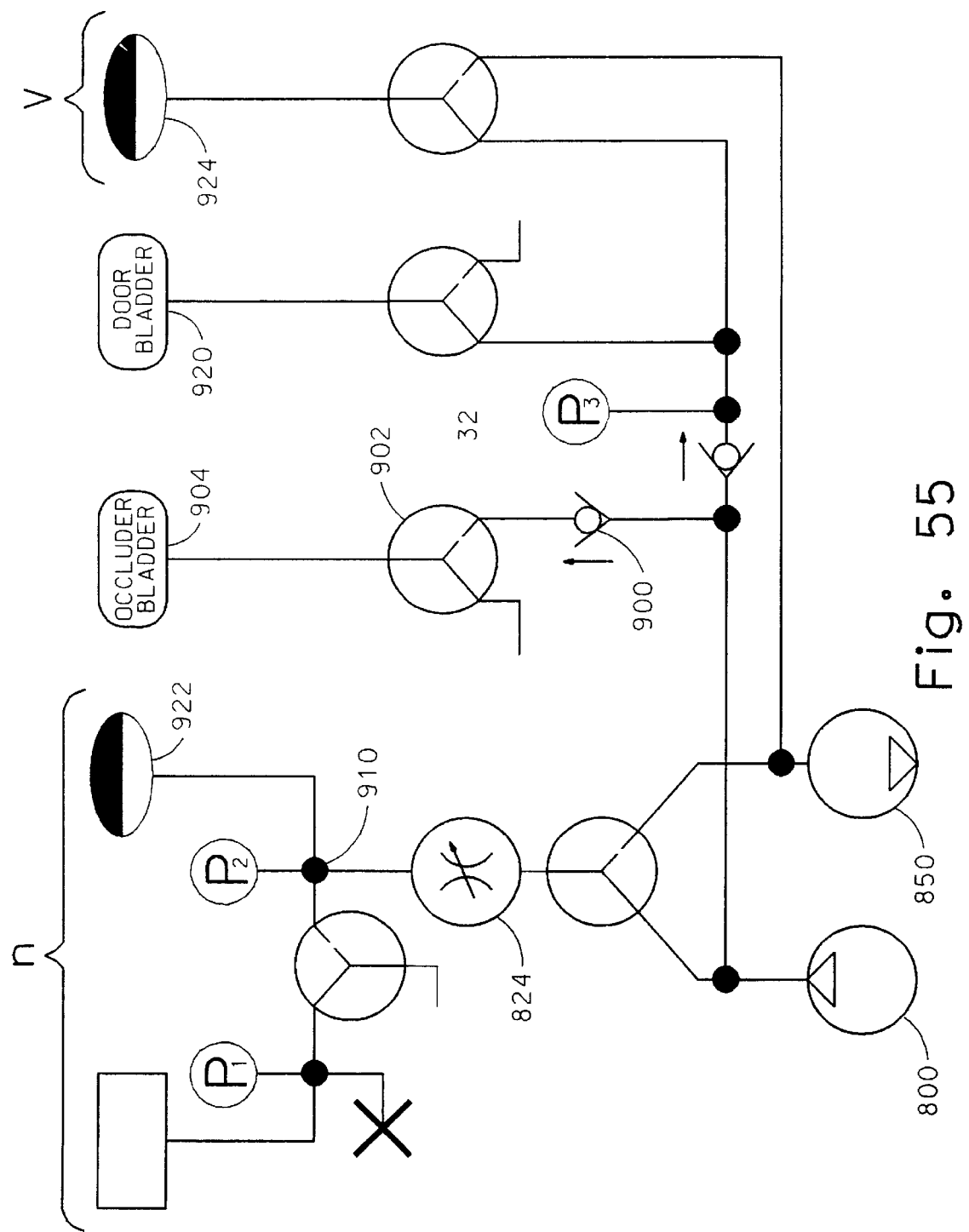
FIG. 55 is a schematic diagram of an exemplary portion of the pneumatic circuit shown in FIG. 54.

In a first alternative embodiment of the pressure distribution system as may best be seen in FIGS. 54 and 55, a compressor 800 delivers high pressure air to a line 802 which is then fed via a check valve 804 to a door bladder valve 806 and a volumetric measurement valve 808. The door bladder 812 is connected to the valve 806 to be pressurized therefrom and a door bladder pressure transducer 820 measures the pressure of the door bladder. The high pressure air is also supplied to a selector valve 822 which feeds a flow proportional valve 824 adapted to receive above atmospheric pressure air which is supplied by a pump line 826 to the pump actuator PA1. Unregulated or raw high pressure air is supplied to a high pressure manifold 830 and supplied to a pair of valve actuator manifolds 832 and 834 for delivery of high pressure air to the valve actuators VA1 through VA10 in the manner of the previous embodiment. A vacuum pump 850 supplies below atmospheric pressure to selector valve 822 and a selector valve 852.

A second flow proportional valve 853 is connected thereto for delivery of selected pressure vacuum over a line 854 to the pressure actuator PA2. Raw vacuum is supplied to a line 860 which is distributed to the valve assemblies 832 and 834 for delivery to the valve actuators when selected by one or more of the plurality of valves 832 and 834. An occluder bladder is also connected to receive high pressure air and the system acts in a fashion similar to that of the previous pressure regulator system except that it relies on only two flow proportional valves 824 and 852 rather than four flow proportional valves and hence is less expensive to manufacture.

An exemplary portion of that type of system is shown in FIG. 55, using only a single flow proportional valve with high pressure connected through a check valve 900 to a selector valve 902 and to an occluder bladder 904 and having a flow and pressure measurement system 910 connected thereto. A door bladder 920 receives high pressure air from the compressor 800 and a pressure actuation chamber 922 can receive either high or low pressure air from the flow proportional valve 824. A valve actuator 924 is connected to receive unregulated high or low pressure air. The system is relatively simple and requires only a relatively small number of parts to achieve the pressure profiling provided by the previous embodiments.

Figure 6:
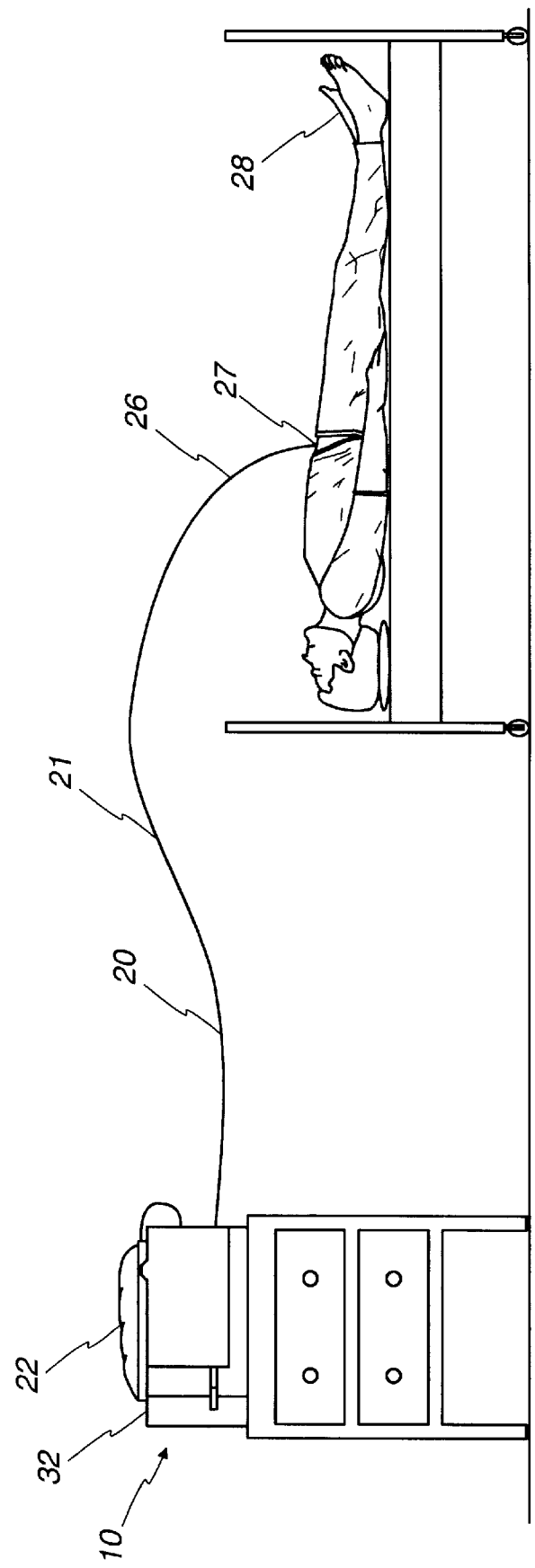
FIG. 6 is an elevational view of the automated peritoneal dialysis apparatus of FIG. 1 in operative connection with a patient being dialyzed.
Figure 7:
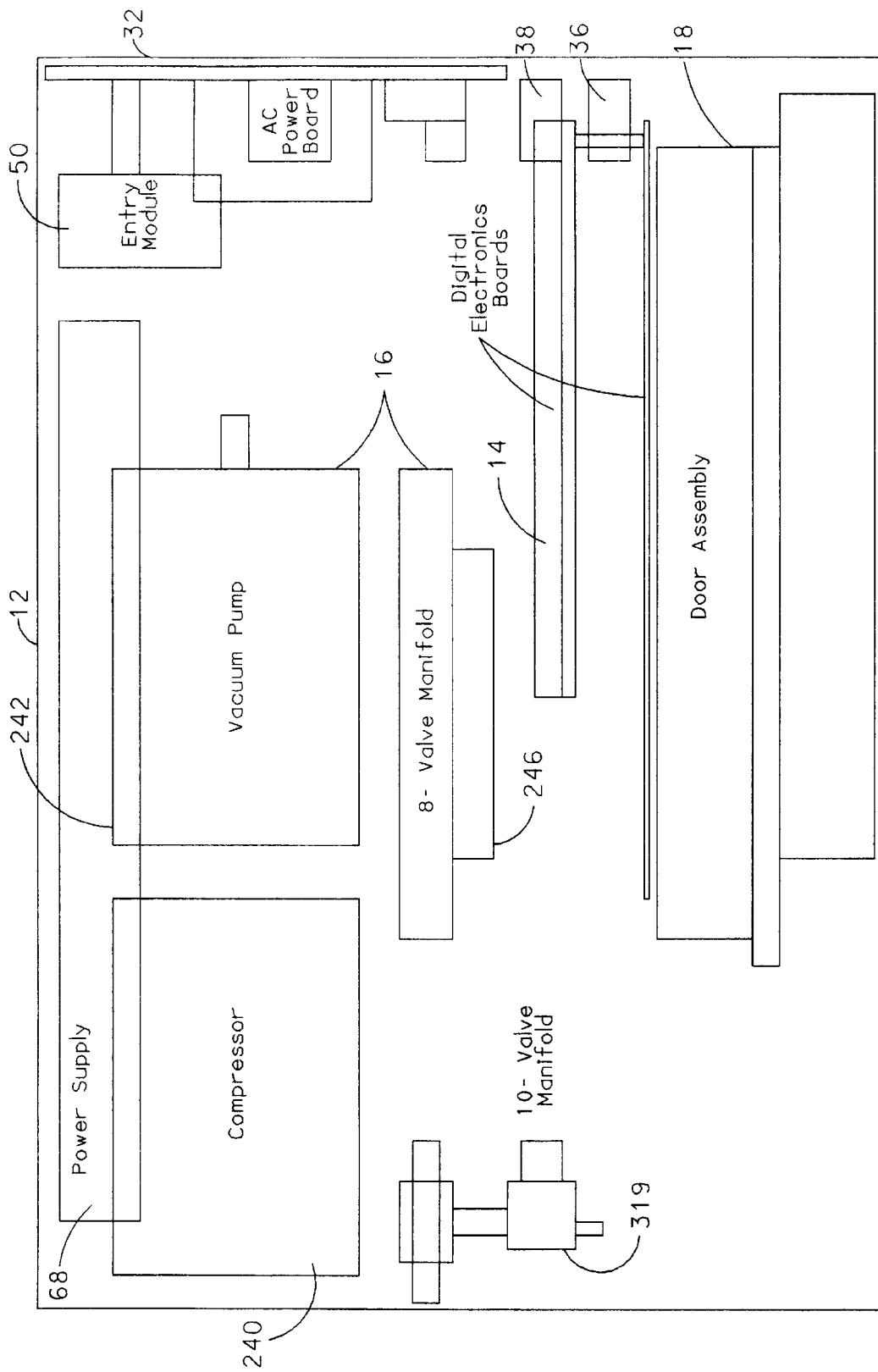
FIG. 7 is a schematic mechanical layout of the components of the APD system shown in FIG. 1.
Figure 8:
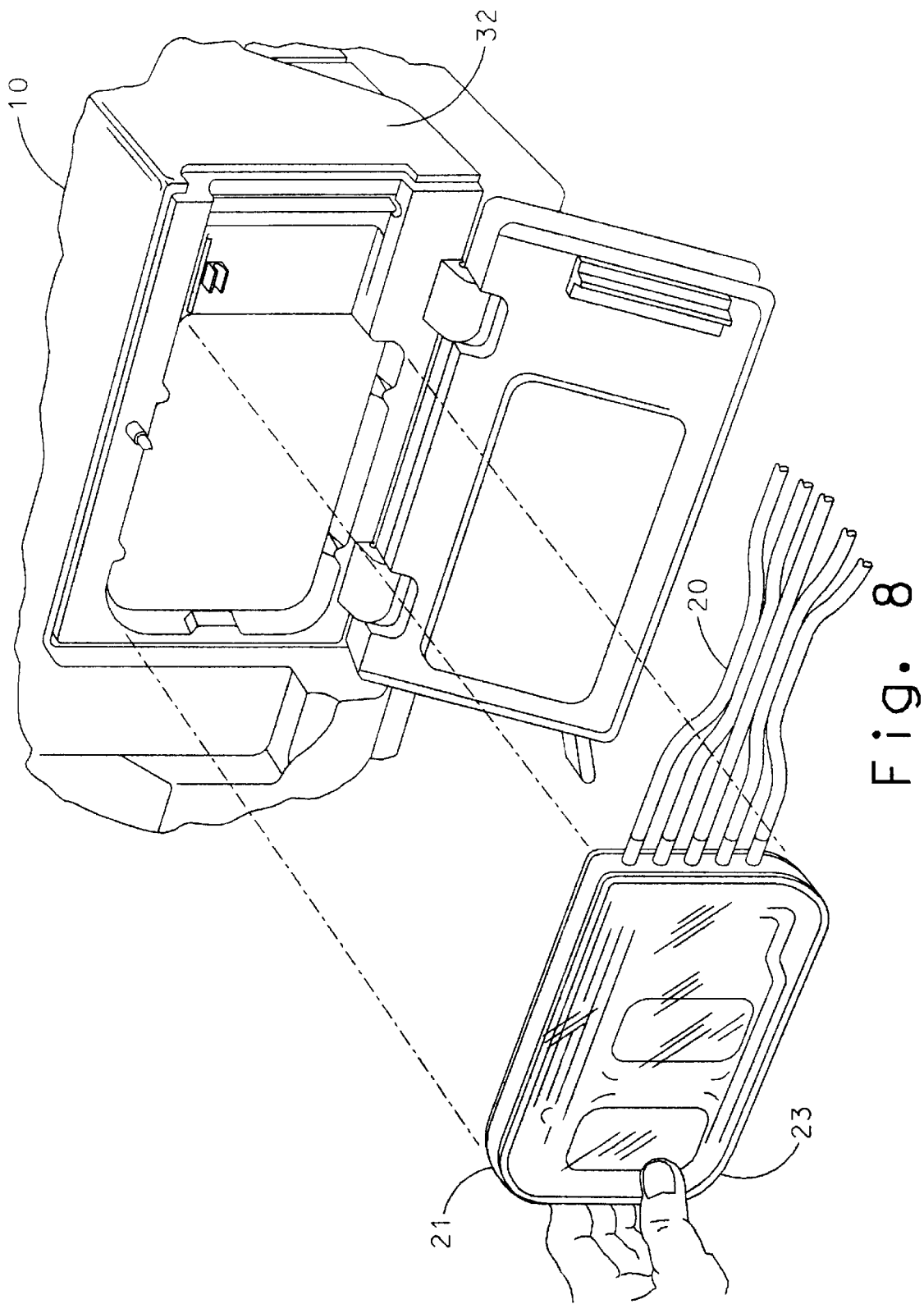
FIG. 8 is a partially exploded, fragmentary, perspective view showing the cassette holder of the APD system shown in FIG. 1 and a disposable dialysate cassette in relation thereto.
Figure 9:
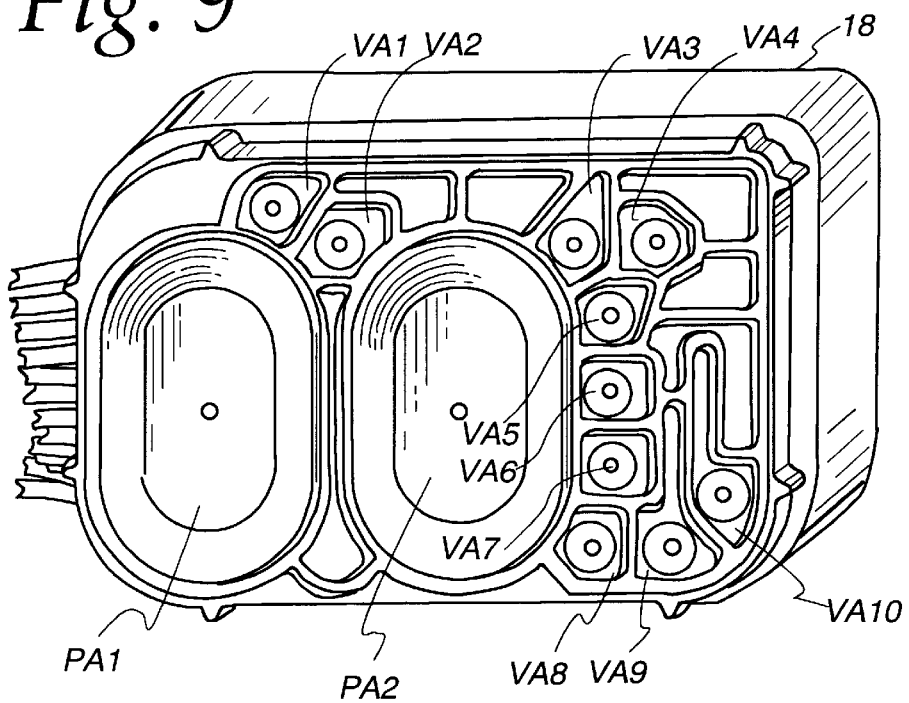
FIG. 9 is a rear elevational view of a pneumatic interface of the APD system shown in FIG. 1.

A third embodiment of a pressure distribution system, as may best be seen in FIG. 6, includes a compressor or pressure source 1000 and a vacuum source 1002 connected to respective bleed valves 1004 and 1006, which are vented. A bleed valve 1008 couples pressure to an occluder bladder 1010 and another bleed valve 1012 couples pressure to a door bladder 1014. A negative pressure reservoir 1016 is provided, which is in communication through the valve 106 with the vacuum pump 1002 and the door bladder and the negative pressure reservoir are in communication via a selector valve 1020 with a valve actuator 1022. A selector valve 1024 couples either vacuum or positive pressure to a flow proportional valve 1026 which supplies flow at a measured pressure to a pump actuator 1030.

A pressure measuring system 1040, including a reservoir 1042, is coupled to the pump chamber 1030 to measure the amount of fluid displaced thereby. The system is relatively simple in that a single flow proportional valve is able to do double duty for both pressure and vacuum strokes for a disposable pump chamber.

Figure 56:
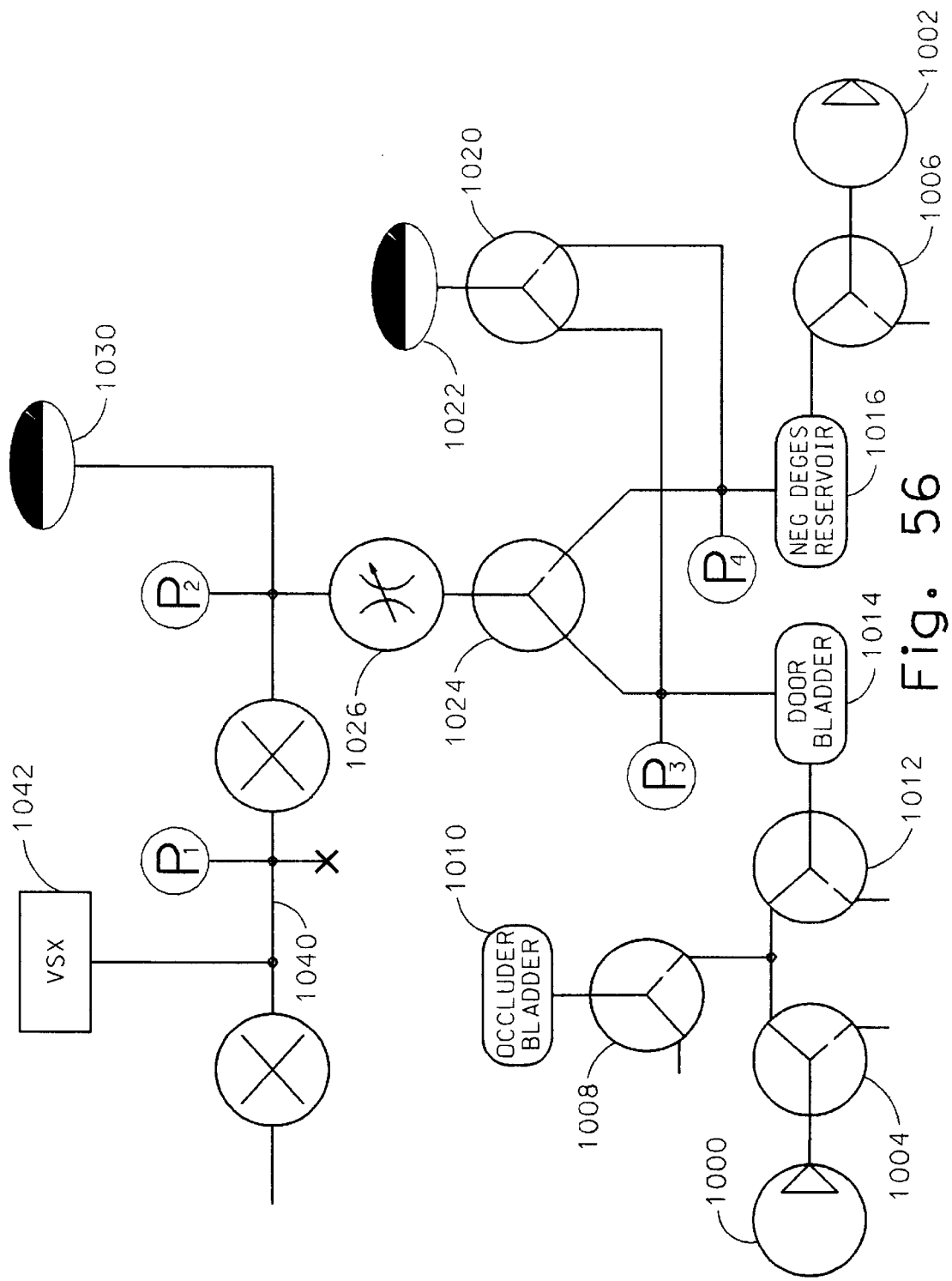
FIG. 56 is a schematic diagram of a third embodiment of an alternative simplified pneumatic distribution assembly.
Figure 57:
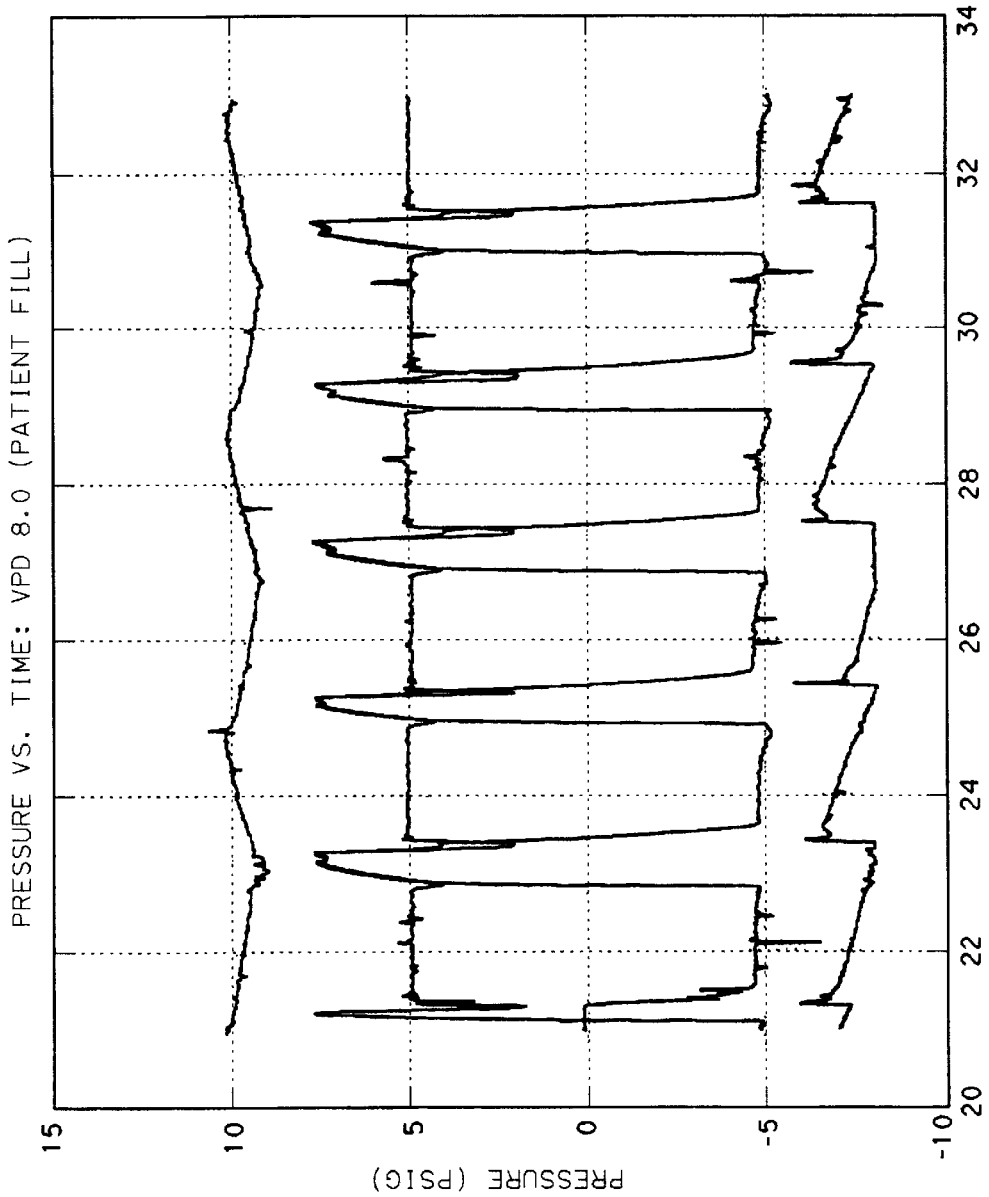
FIG. 57 is a graph of a plurality of operating pressures with respect to time during an in-vitro dialysate fill cycle using the pneumatic distribution assembly shown in FIG. 56.
Figure 58:
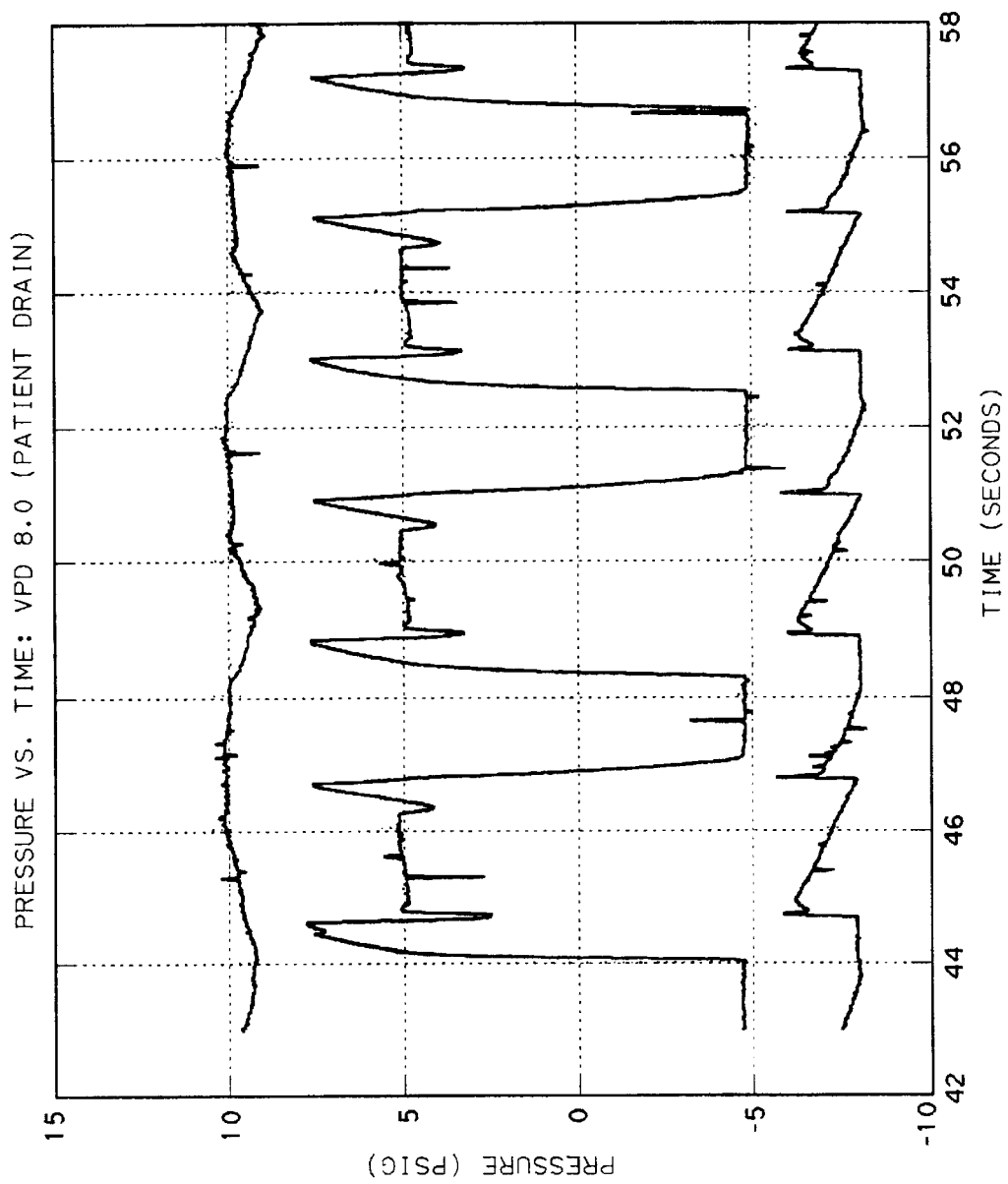
FIG. 58 is a graph of a plurality of operating pressures with respect to time during an in-vitro dialysate drain cycle using pneumatic distribution assembly shown in FIG. 56.

Operation of the system set forth in FIG. 56 is evidenced by the pressure graph shown in FIG. 57 wherein the lowest most curve is an indicator of the vacuum source pressure; the second lowest curve is an indicator of chamber pressure at a right pump chamber; the uppermost curve is an indicator of pressure from the positive supply or compressor and the curve which is the second from the top in the chamber is indicative of the left pump chamber. A similar curve is shown for only a single pump chamber with the upper and lower curves being for the positive and negative pressure sources and the middle curve being taken at the pump chamber as may best be seen in FIG. 58.

Figure 59:
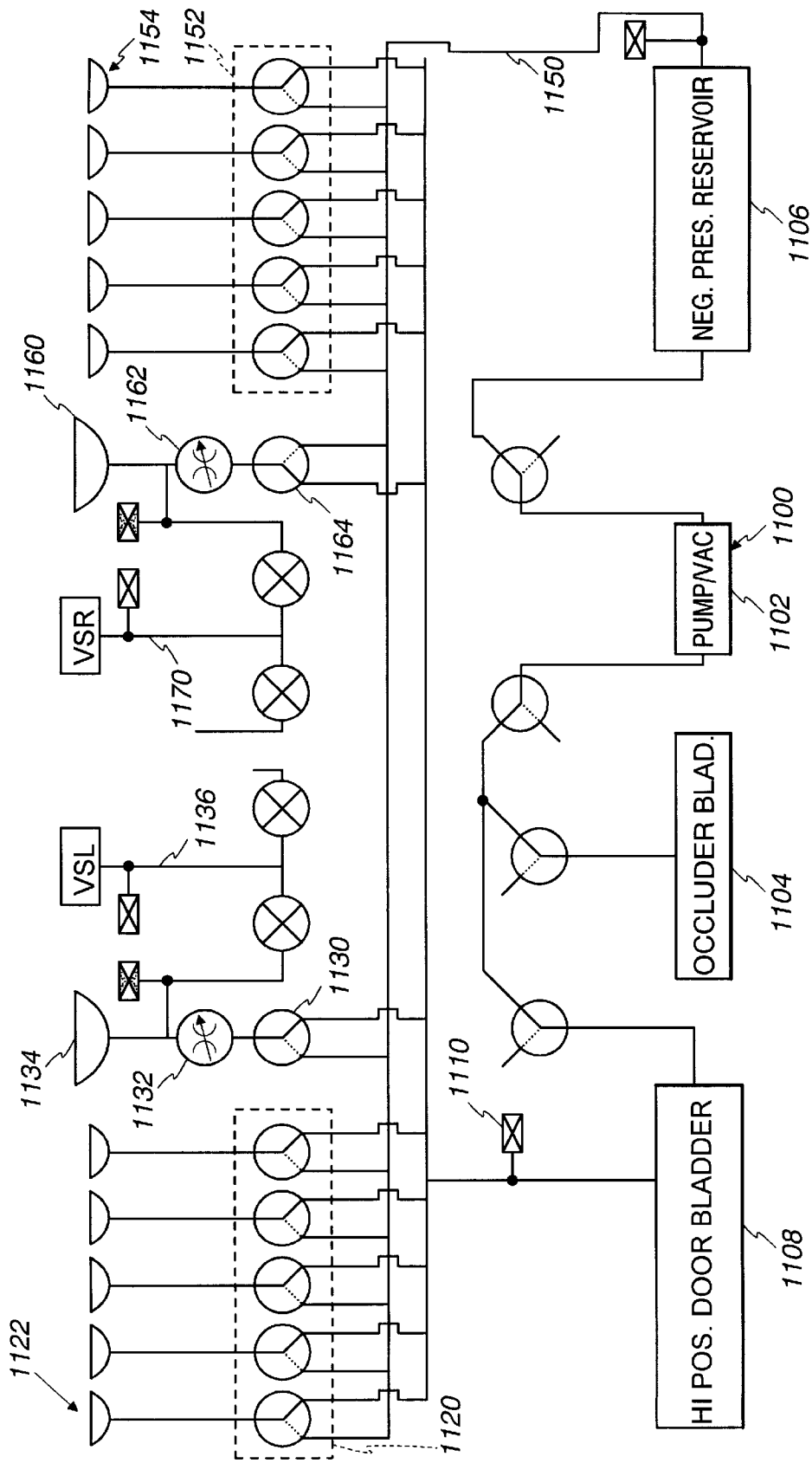
FIG. 59 is a schematic diagram of a fourth embodiment of a pneumatic system for use with the APD system shown in FIG. 1.

A still further embodiment of the system includes a pressure regulator system 1100 as may best be seen in FIG. 59. The pressure regulator system 1100 includes a combination compressor and vacuum pump 1102 coupled to an occluder bladder 1104 and a negative pressure reservoir 1106. A high pressure door bladder 1108 is coupled and parallel with the occluder bladder and has a pressure transducer 1110 connected thereto. A plurality of three-way selector valves 1120 are connected to a plurality of valve actuators 1122 comprising a portion of a pneumatic interface. A selector valve 1130 is coupled to a flow proportional valve 1132, which is in turn coupled to a pump actuator 1134. A flow measurement system 1136 is connected thereto. The negative pressure reservoir is connected via a line 1150 both to the first set of selector valves 1120 and a second set of selector valves 1152. The second set of selector valves 1152 operates and delivers air or vacuum to a plurality of valve actuators 1154. A pump actuator 1160 is driven through a flow proportional valve 1162 which receives either positive or negative pressure via a selector valve 1164 from the negative pressure reservoir or from the high positive pressure door bladder. This system too is able to achieve pressure profiling with a minimum number of components and reservoirs. A flow measuring system 1170 is connected to the pump actuator 1160 to provide a flow measurement indication back to the computer.

Various features of the invention are set forth in the following claims.

What is claimed is:

1. A system for performing peritoneal dialysis on a patient comprising:
    a) a liquid pump operated by fluid pressure to cause liquid to flow to and from a peritoneal cavity of a patent;
    b) a fluid conduit to and from the liquid pump for providing fluid to operate the liquid pump;
    c) a vacuum source for communicating negative pressure to the conduit and to the liquid pump to draw liquid into the liquid pump;
    d) a positive pressure source for communicating positive pressure to the conduit and to the liquid pump to expel liquid from the liquid pump; and
    e) a fluid distribution system including a flow proportional valve to control flow rate and pressure of the fluid through the fluid conduit from the respective pressure and vacuum sources to operate the liquid pump to cause liquid to be pumped into and from the peritoneal cavity.

2. A system for performing peritoneal dialysis on a patient according to claim 1 wherein the fluid distribution system comprises a selector valve for selectively connecting the vacuum source or the positive pressure source to the liquid pump.

3. A system for performing peritoneal dialysis on a patient according to claim 2 wherein the liquid pump comprises a diaphragm pump having a diaphragm and a fluid chamber, and the fluid distribution system further comprises a second flow proportional control valve and a second selector valve, each fluid chamber communicating with one of the flow proportional valves and one of the selector valves.

4. A system for performing peritoneal dialysis on a patient according to claim 1 wherein the fluid distribution system further comprises a second flow proportional control valve and a pump chamber.

5. A system for performing peritoneal dialysis on a patient according to claim 1 further comprising a liquid occluder for stopping liquid flow to or from a peritoneal cavity of the patient, said liquid occluder being connected to said fluid distribution system and operated thereby; and a valve in said fluid distribution system for allowing air flow from the occluder to render the occluder operative when the system is disabled to prevent liquid flow.

6. A liquid pumping system, comprising:
    a) a first liquid pump having a diaphragm;
    b) a second liquid pump having a diaphragm;
    c) a fluid distribution system for driving each liquid pump, having
        (i) selector valve means,
        (ii) flow proportional means,
        (iii) conduit means between the selector valve means and the flow proportional means and the first and second liquid pumps;
    d) a source of positive pressure fluid for expelling liquid from each liquid pump; and e) a source of vacuum fluid for drawing liquid into each liquid pump.

7. A liquid pumping system according to claim 6 further comprising a plurality of liquid valves in communication with the first and second liquid pumps and a plurality of actuator valves for receiving positive pressure fluid and vacuum fluid from the sources of positive pressure fluid and vacuum fluid for liquid valves connected to and operated by the fluid distribution system.

8. A liquid pumping system, comprising:

a pump having a diaphragm defining a liquid chamber;

a liquid input conduit for transporting liquid to the liquid chamber of the pump;

a liquid output conduit for transporting liquid from the liquid chamber of the pump;

a positive pressure fluid source for supplying fluid at a pressure greater than atmospheric pressure to the diaphragm of the pump to drive the diaphragm to expel liquid from the liquid chamber;

a negative pressure fluid source for supplying fluid at a pressure less than atmospheric pressure to the diaphragm of the pump to drive the diaphragm to draw liquid into the liquid chamber; and pressure regulating means operatively connected to the positive and negative pressure fluid sources for regulating the flows of positive pressure fluid and negative pressure fluid to the diaphragm of the pump to provide a pressure regulated drive of the diaphragm.

9. A liquid pumping system according to claim 8 wherein the pressure regulating means comprises:

a first control valve between the positive pressure fluid source and the diaphragm; and a second control valve between the negative pressure fluid source and the diaphragm;

wherein each of said first and second control valves can be opened to varying amounts to regulate fluid flow between the fluid sources and the diaphragm.

10. A liquid pumping system according to claim 9, wherein the positive pressure fluid source comprises a first compressor connected directly to the diaphragm without a reservoir therebetween; and wherein the negative pressure fluid source comprises a second compressor connected directly to the fluid chamber without a reservoir therebetween.

11. A liquid pumping system according to claim 9, wherein the positive pressure control valve and the negative pressure control valve are each opened varying amounts at the same time to regulate fluid flow to and from the diaphragm.

12. A liquid pumping system according to claim 9, further comprising a pressure sensor for sensing the pressure being supplied at the diaphragm.

13. A liquid pumping system according to claim 9, wherein a pressure regulating circuit closes the negative pressure flow control valve when the positive pressure flow control valve is opened and closes the positive pressure flow control valve when the negative pressure control valve is opened.

14. A liquid pumping system according to claim 8, further comprising:

a first liquid valve in the liquid input conduit leading into the liquid chamber, and a second liquid valve in the liquid output conduit leading away from the liquid chamber.

15. A liquid pumping system according to claim 9, wherein the first and second liquid valves each have a valve diaphragm and a liquid chamber, the valve chambers being separated by the valve diaphragm, the aforementioned elements operating in cooperation to control liquid flow through each valve; and further comprising a plurality of fluid conduits extending from the positive pressure fluid source and the negative pressure fluid source to the fluid chambers of the respective valves.

16. A liquid pumping system according to claim 15, further comprising a check valve positioned in the conduit between the positive pressure source and the liquid control valves to prevent positive pressure fluid from moving back into the positive pressure fluid source.

17. A liquid pumping system according to claim 15, wherein each of the liquid flow control valves comprises a raised valve seat which cooperates when engaged by the valve diaphragm stops liquid flow therethrough and which when displaced from the valve seat allows liquid to flow between the valve seat and the diaphragm.

18. A liquid pumping system according to claim 15 wherein each liquid flow control valve is actuated by air controlled by a three-way valve, the three-way valve communicating either positive pressure air or negative pressure air to the fluid valve chamber in order to seat or unseat the valve diaphragm, respectively.

19. A peritoneal dialysis system, comprising:

a pair of diaphragm pumps, each diaphragm pump of the pair of diaphragm pumps having a diaphragm defining a liquid chamber, each liquid chamber having an inlet and an outlet;

a plurality of liquid conduits, each liquid conduit of the plurality being operatively connected to at least one of the diaphragm pumps for providing a liquid input to or a liquid output from the liquid chamber of the respective diaphragm pump;

a positive pressure fluid source for supplying fluid at a first pressure greater than atmospheric pressure to the fluid chamber of the pump to drive the diaphragm to expel liquid from the liquid chamber of the pump;

a negative pressure fluid source for supplying fluid at a second pressure less than atmospheric pressure to the fluid chamber of the pump to drive the diaphragm to draw liquid into the liquid chamber of the pump;

pressure regulating means for regulating fluid flow between the fluid sources and the fluid chambers of the pumps;

a plurality of liquid valves, each liquid valve being associated with one or more of the liquid conduits, whereby actuation of a selected liquid valve will permit liquid to flow through the liquid valve; and selector/actuator means for each liquid valve for selecting either positive pressure fluid or negative pressure fluid for actuation of each liquid valve.

20. An actuator system for actuating of a plurality of liquid valves and at least two liquid pumps, each liquid pump having a diaphragm defining a liquid chamber, comprising:

a positive pressure fluid source;

a negative pressure fluid source;

a pair of variable pressure fluidic actuators for each liquid pump, each actuator including a first control valve between the positive pressure fluid source and the diaphragm, and a second control valve between the negative pressure fluid source and the diaphragm, wherein each of said first and second control valves can be opened to varying amounts to regulate fluid flow between the fluid sources and the diaphragm; and selector/actuator means for each liquid valve for selecting either positive pressure fluid or negative pressure fluid for actuation of the liquid valve.

21. An actuator system for fluidic actuation of a plurality of liquid valves and at least two liquid pumps, each liquid pump having a diaphragm defining a driven liquid chamber and a driving fluid chamber, comprising:

a positive pressure fluid source;

a negative pressure fluid source;

a fluid distribution network for distributing fluid between the fluid sources and the fluidic actuators;

a variable pressure fluidic actuator for each liquid pump, including a selector valve for selecting from either the positive pressure fluid source or the negative pressure fluid source and a control valve between the selected fluid source and the fluid chamber, wherein said control valve can be opened to varying amounts to regulate fluid flow between the fluid source and the fluid chamber; and selector/actuator means for each liquid valve for selecting either positive pressure fluid or negative pressure fluid for actuation of the liquid valve.

22. An automated peritoneal dialysis system for supplying dialysate to a peritoneal cavity of a patient, comprising:

a controller for generating a valve control signal in response to a command signal and to a pressure feedback signal;

a pneumatic pressure distribution system for control by the controller and having a flow adjustable valve for supplying air to an air delivery channel in response to the valve control signal, said pneumatic pressure distribution system having a pressure sensor for producing the pressure signal in response to the pressure of the air supplied by the flow adjustable valve;

a pressure signal feedback channel coupling the pressure signal to the controller; and a cassette interface for receiving a dialysate handling disposable cassette of a disposable liquid delivery set, said cassette interface having a diaphragm pump station connected to the flow adjustable valve for receiving air therefrom, the received air being for supply to a diaphragm of a diaphragm pump of the disposable cassette for driving the diaphragm pump to pump dialysate through other portions of the disposable liquid delivery set for delivery to a peritoneal cavity of a patient.

23. A dialysate delivery system, comprising:

a dialysate cassette interface for pneumatic coupling to a disposable dialysate cassette having a plurality of pneumatically controlled dialysate valves and a dialysate diaphragm pump, the dialysate cassette interface having a plurality of pneumatically driven cassette valve actuators for coupling with respective ones of the pneumatically controlled cassette dialysate valves and a diaphragm pump drive station for coupling to the dialysate diaphragm of the dialysate cassette;

a controller for generating a plurality of pneumatic valve control signals and for generating a diaphragm pump pressure control signal responsive to a received pressure signal; a plurality of on-off valves responsive to the pneumatic valve control signals to provide selected pneumatic control forces to the pneumatically driven cassette valve actuators of the cassette interface;

an adjustable pneumatic valve responsive to the pressure control signal to throttle a pneumatic source, resulting in a pneumatic feed to the diaphragm pump drive station of the cassette interface; and a pressure transducer for producing a pressure signal in response to the pneumatic feed.

* * * * *

UNITED STATES PATENT AND TRADEMARK OFFICE
CERTIFICATE OF CORRECTION

PATENT NO. : 5,938,634
DATED : August 17, 1999
INVENTOR(S) : Warren J. Packard

It is certified that error appears in the above-identified patent and that said Letters Patent is hereby corrected as shown below:

Column 11, Line 35: delete "Pi" and insert --P1--

Signed and Sealed this

Second Day of May, 2000

Attest:

Q. TODD DICKINSON

*Attesting Officer*     *Director of Patents and Trademarks*